US012708278B2

(12) United States Patent
Matsumura et al.

(10) Patent No.: US 12,708,278 B2

(45) Date of Patent: Aug. 18, 2026

(54) BIOLOGICAL SIGNAL MEASUREMENT DEVICE, METHOD, AND NON-TRANSITORY STORAGE MEDIUM STORING PROGRAM

(71) Applicant: OMRON HEALTHCARE Co., Ltd., Kyoto (JP)

(72) Inventors: Naomi Matsumura, Kyoto (JP); Yasuhiro Kawabata, Kyoto (JP); Kenji Fujii, Kyoto (JP); Reiji Fujita, Kyoto (JP); Akito Ito, Kyoto (JP); Yuki Sakaguchi, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 782 days.

(21) Appl. No.: 17/819,822

(22) Filed: Aug. 15, 2022

(65) Prior Publication Data

US 2022/0386882 A1 Dec. 8, 2022

Related U.S. Application Data

(63) Continuation of application No. PCT/JP2021/003510, filed on Feb. 1, 2021.

(30) Foreign Application Priority Data

Feb. 20, 2020 (JP) ................................ 2020-027364

(51) Int. Cl.
*A61B 5/0245* (2006.01)
*A61B 5/00* (2006.01)

(52) U.S. Cl.
CPC .......... *A61B 5/0245* (2013.01); *A61B 5/7282* (2013.01); *A61B 5/74* (2013.01); *A61B 2560/0209* (2013.01)

(58) Field of Classification Search
CPC ........................... A61B 5/0245; A61B 5/7282
See application file for complete search history.

(56) References Cited

U.S. PATENT DOCUMENTS

2014/0364750 A1 12/2014 Brumfield et al.
2015/0112606 A1* 4/2015 He .................... A61B 5/02055 702/19

(Continued)

FOREIGN PATENT DOCUMENTS

CN 1985751 A 6/2007
CN 105380620 A 3/2016

(Continued)

OTHER PUBLICATIONS

Office Action issued Oct. 12, 2024 for Chinese Patent Application No. 202180009680.1.

(Continued)

*Primary Examiner* — Daniel L Cerioni
(74) *Attorney, Agent, or Firm* — Colson Law Group, PLLC

(57) ABSTRACT

While power consumption is suppressed, biological information is measured without fail when a condition of a subject changes. An aspect of the present invention is configured to acquire a biological signal related to a beat of a heart of the subject from a biometric sensor, detect a feature of the biological signal from the biological signal acquired, determine an abnormal change in the feature based on the feature detected and first threshold information set in advance, set an operation mode of the biometric sensor to a continuous operation mode when the abnormal change in the feature is determined, and set the operation mode of the biometric sensor to an intermittent operation mode in a period without the abnormal change.

7 Claims, 17 Drawing Sheets

(56) References Cited

U.S. PATENT DOCUMENTS

| | | | | |
|---|---|---|---|---|
| 2015/0185819 | A1* | 7/2015 | Saito | G16H 40/63 713/323 |
| 2017/0164851 | A1* | 6/2017 | Takahashi | A61B 5/02427 |
| 2019/0015051 | A1* | 1/2019 | Gregg | A61B 5/0245 |
| 2019/0141419 | A1 | 5/2019 | Xu et al. | |
| 2019/0261865 | A1 | 8/2019 | Sawado | |

FOREIGN PATENT DOCUMENTS

| | | | |
|---|---|---|---|
| CN | 110167436 | A | 8/2019 |
| CN | 115023181 | A | 9/2022 |
| JP | H07-327940 | A | 12/1995 |
| JP | 2008-054972 | A | 3/2008 |
| JP | 2014-161441 | A | 9/2014 |
| JP | 2015123300 | A | 7/2015 |
| JP | 2016002119 | A | 1/2016 |
| JP | 5984088 | B2 | 9/2016 |
| JP | 2017104382 | A | 6/2017 |

OTHER PUBLICATIONS

International Search Report issued for International Application No. PCT/JP2021/003510, dated Apr. 20, 2021.

IPRP issues for International Application No. PCT/JP2021/003510, dated Aug. 27, 2021.

International Preliminary Report on Patentability for International Application No. PCT/JP2021/003510, Dated Aug. 25, 2022.

Office Action issued May 13, 2025 for Chinese Patent Application No. 202180009680.1.

* cited by examiner

[FIG. 1]
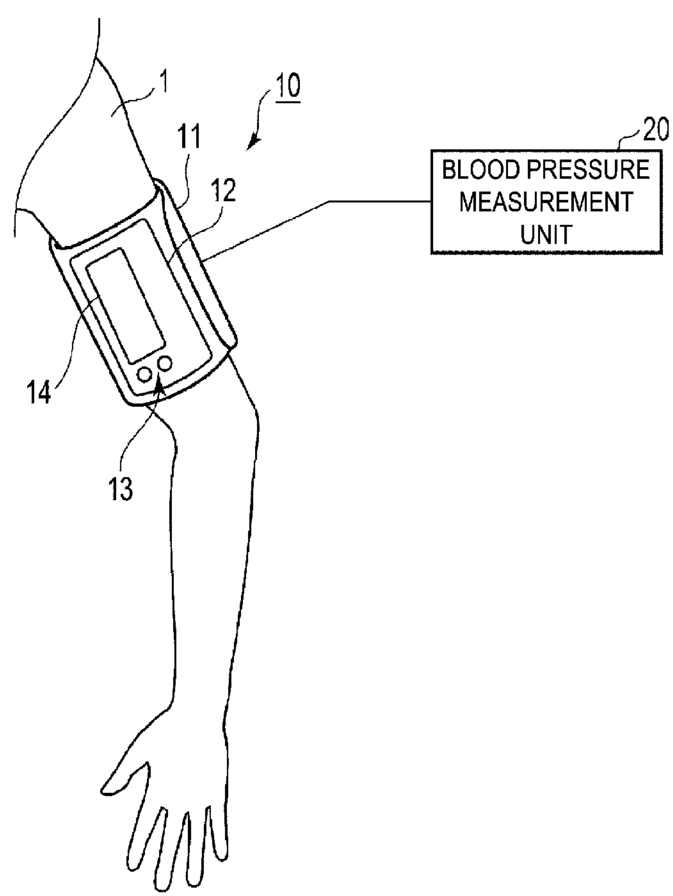
[FIG. 2]
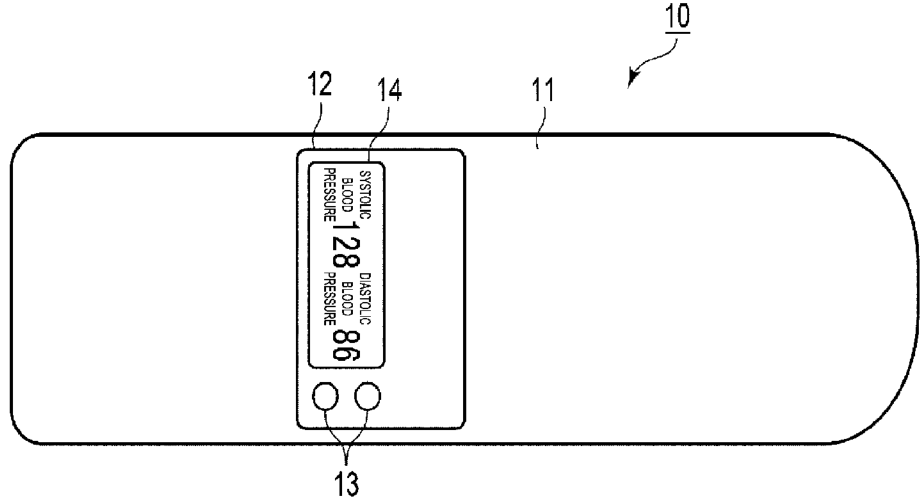

[FIG. 3]
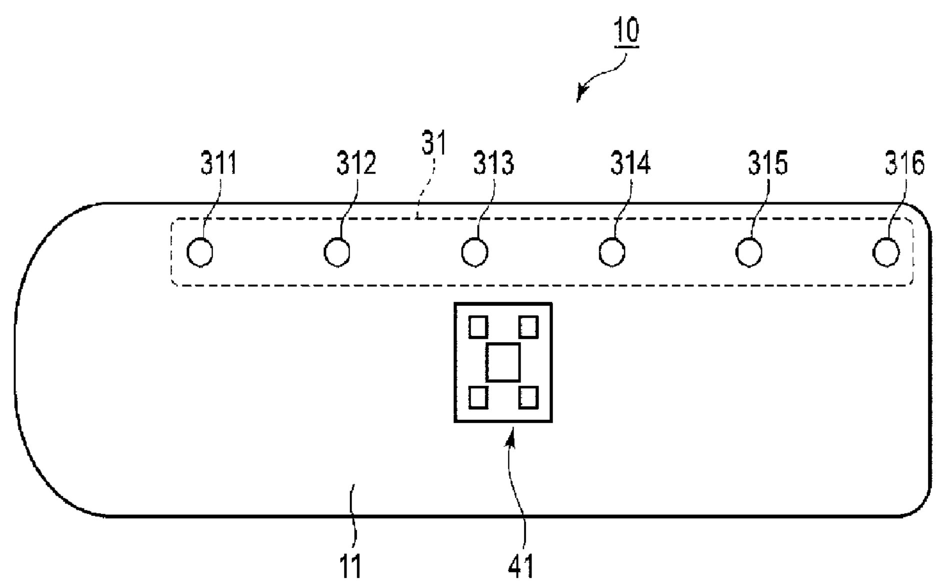
[FIG. 4]
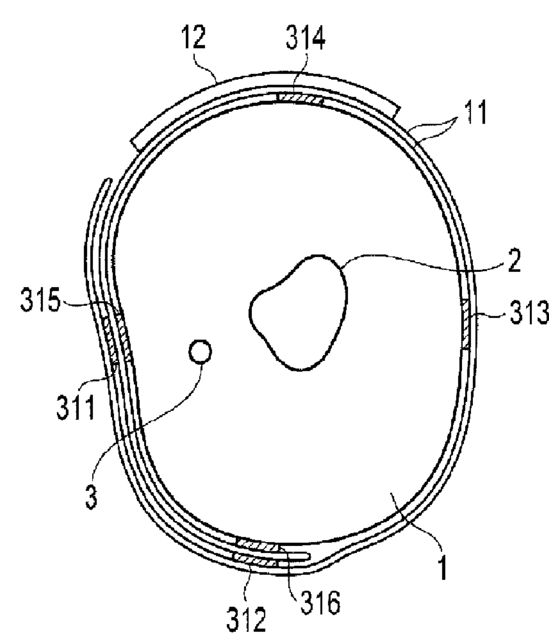

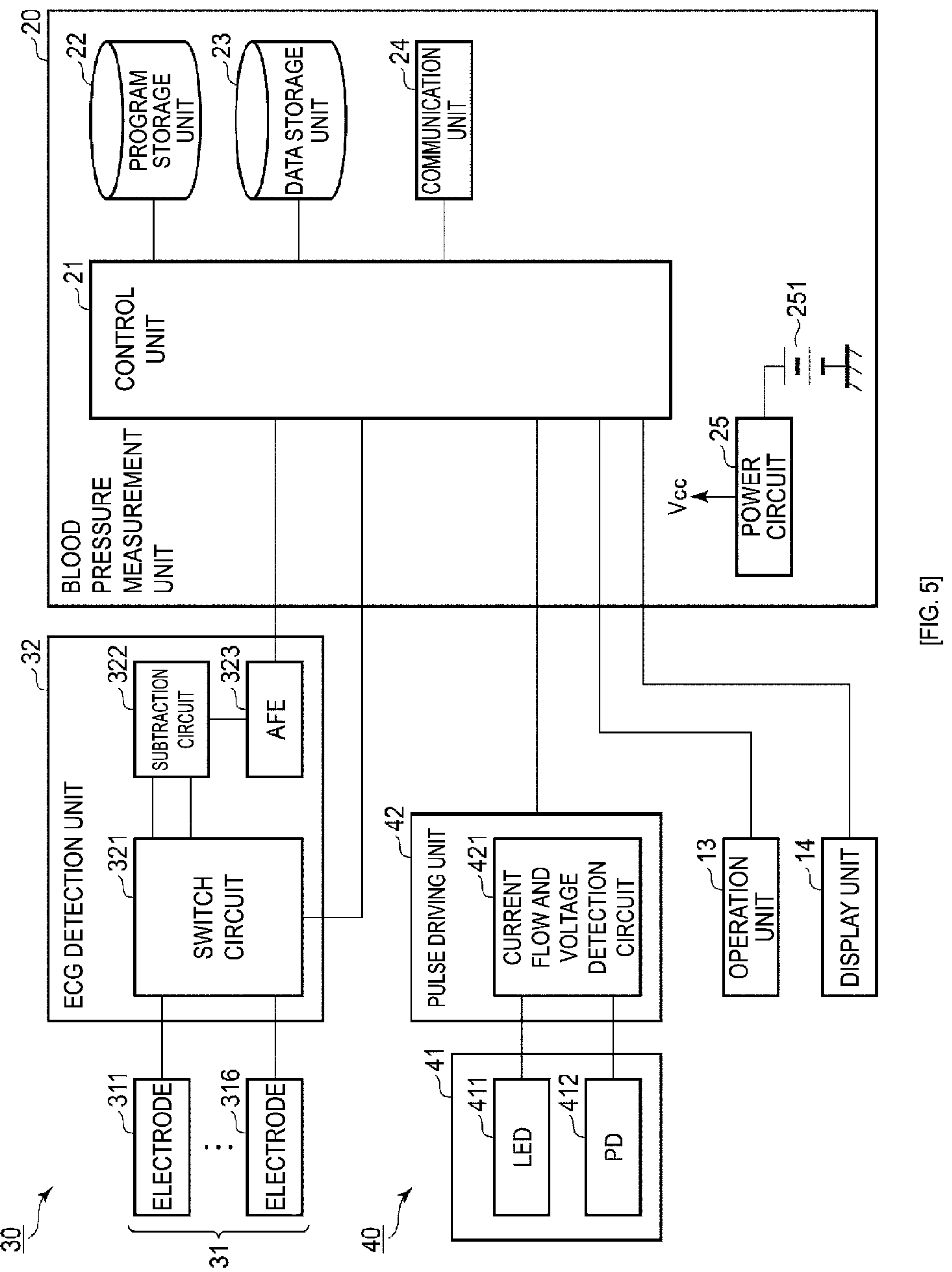
[FIG. 5]

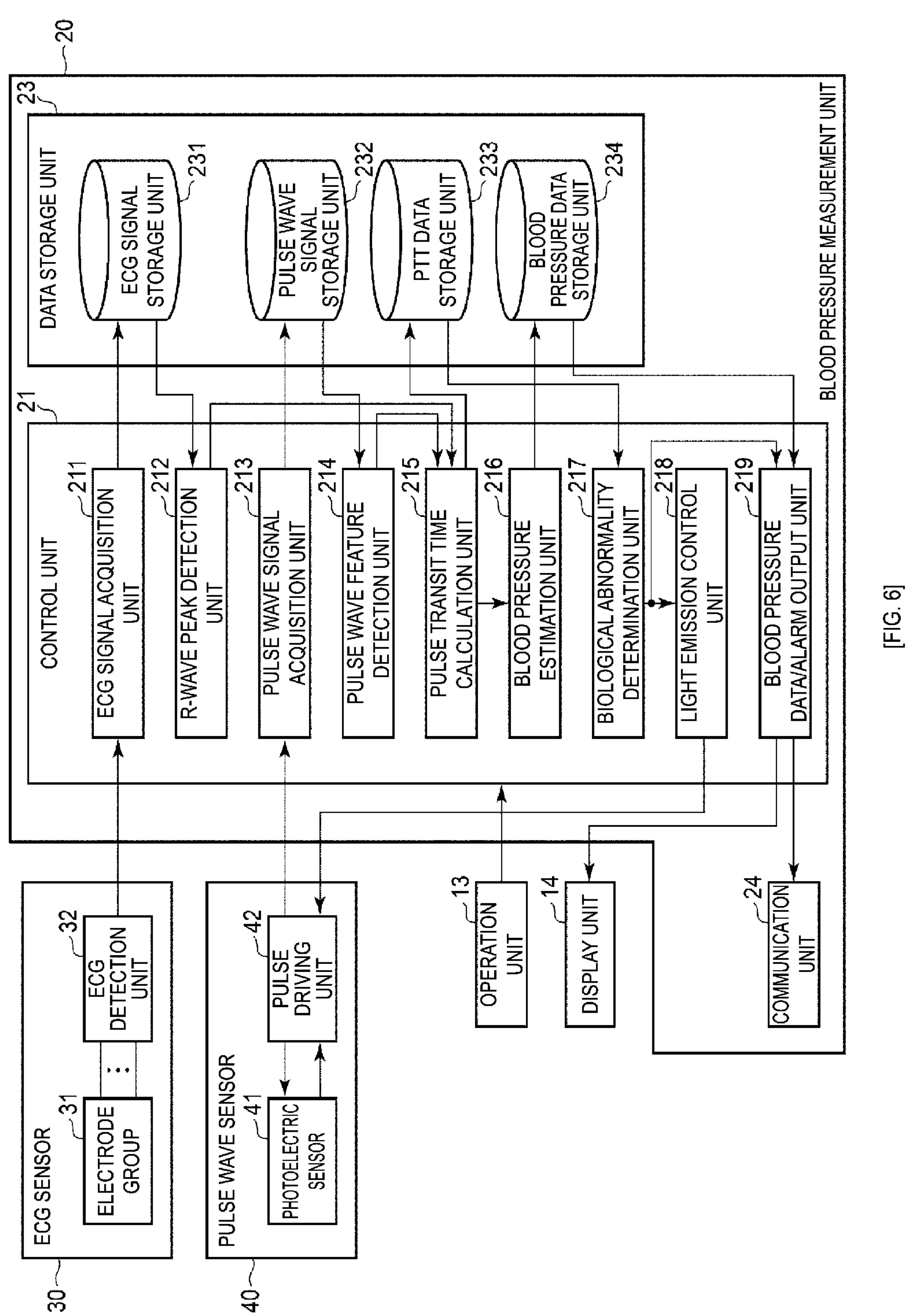
[FIG. 6]

[FIG. 7]
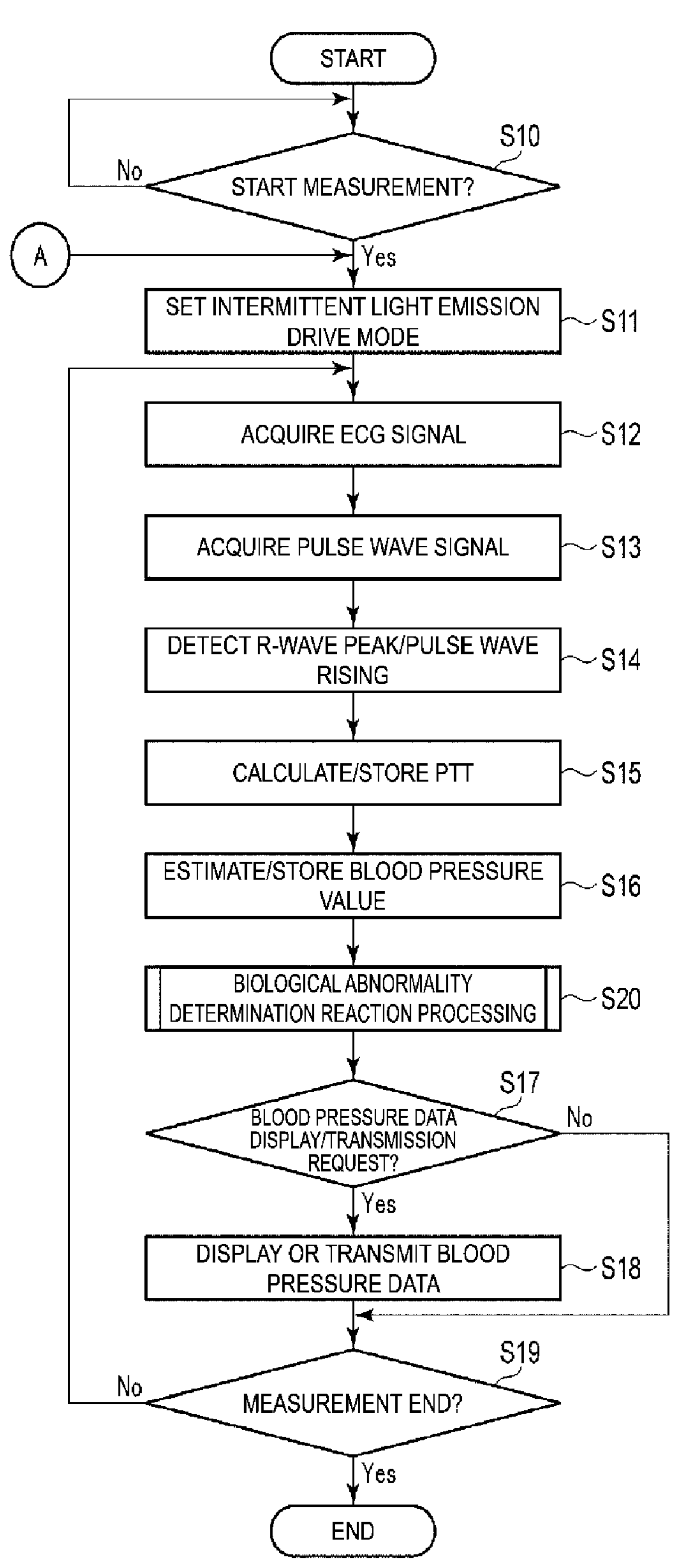

[FIG. 8]
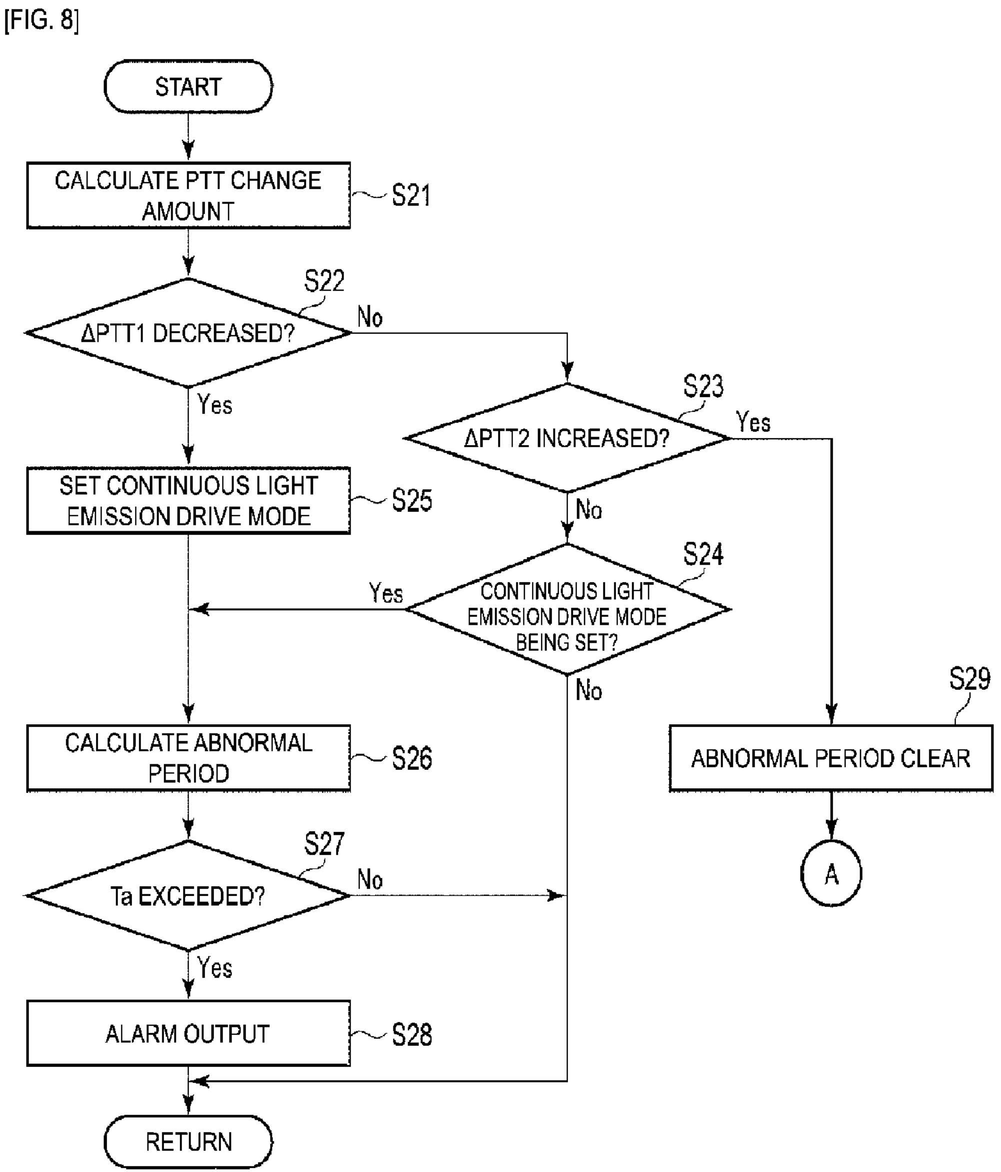

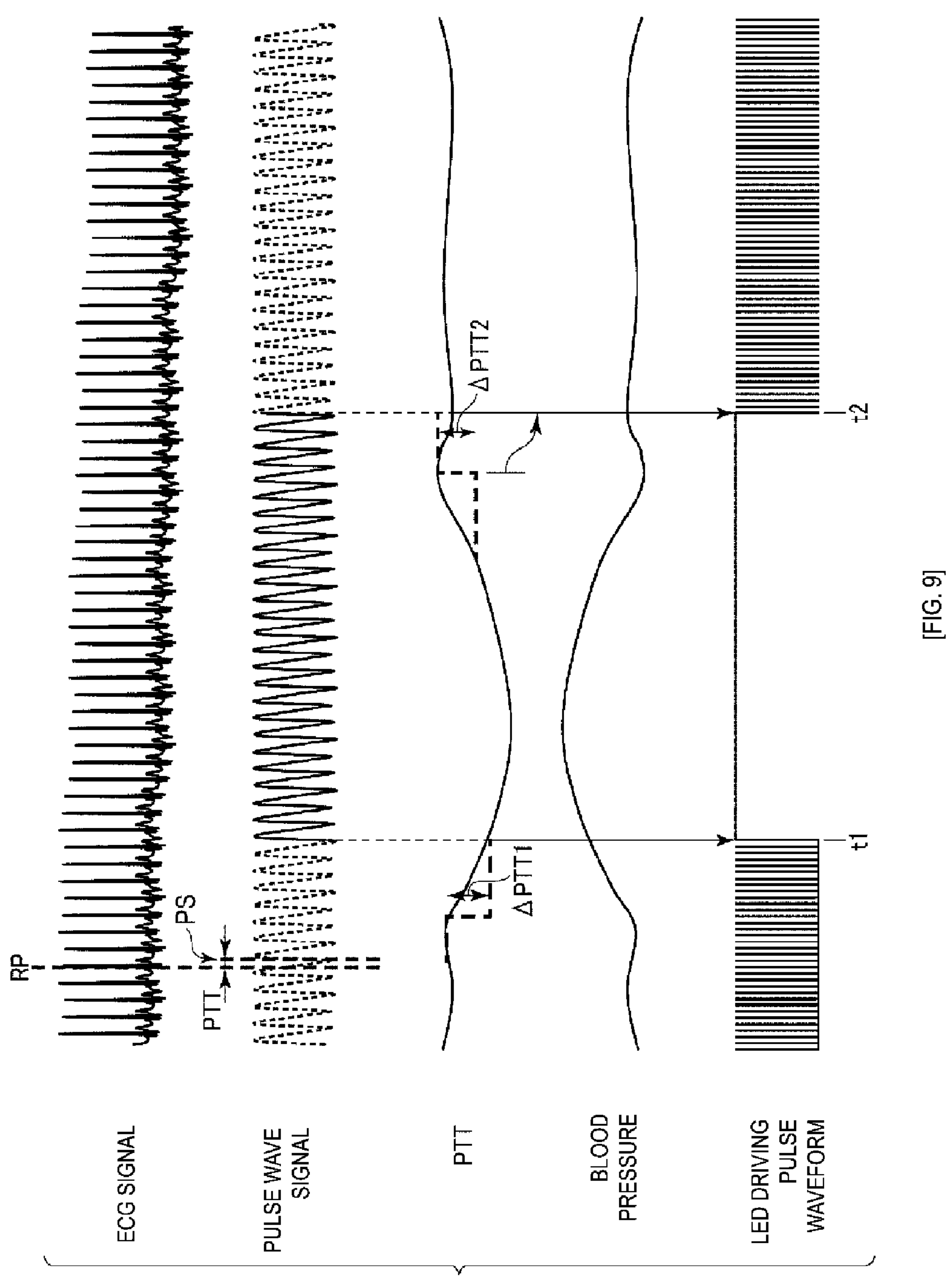
[FIG. 9]

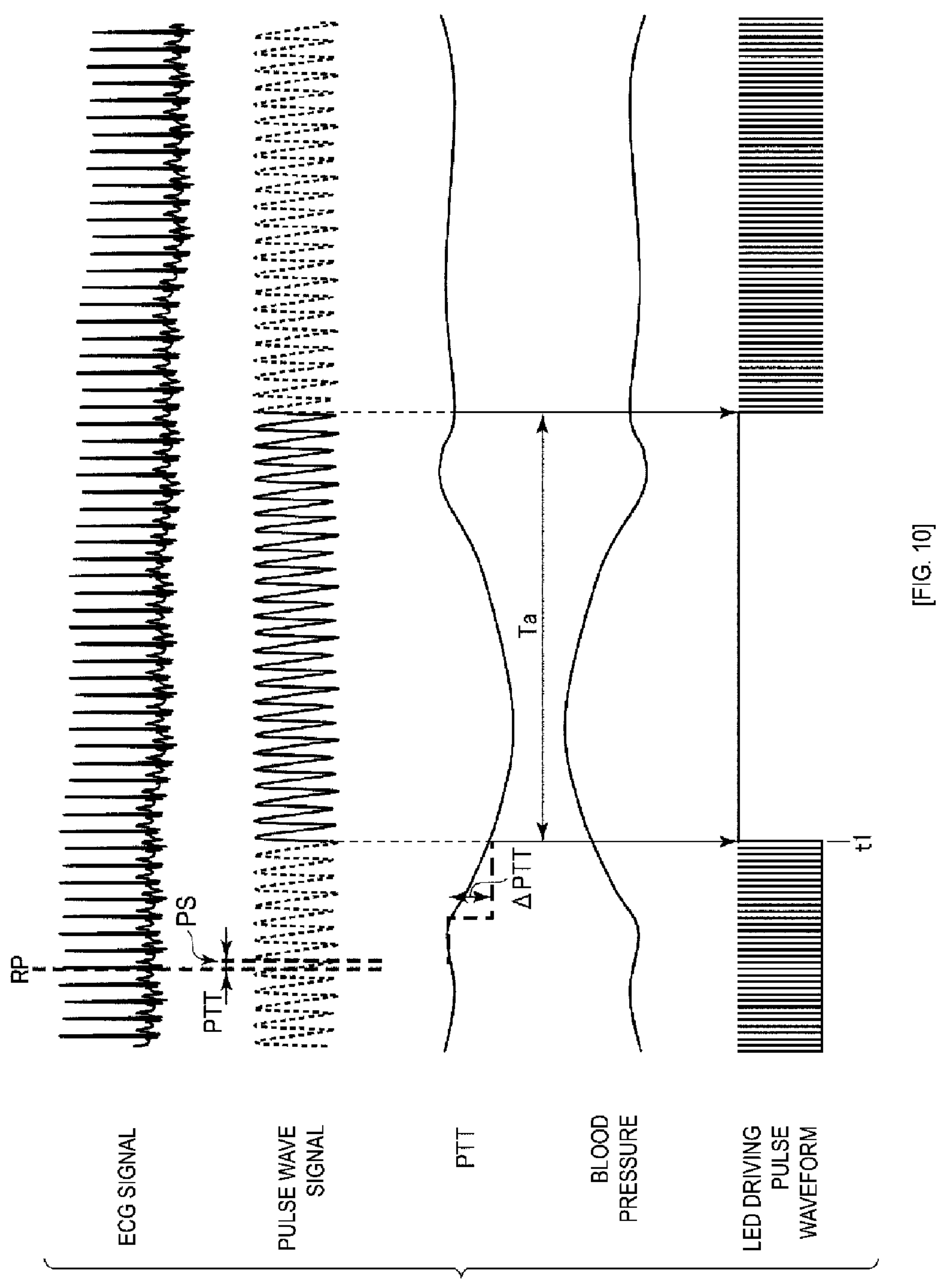
[FIG. 10]

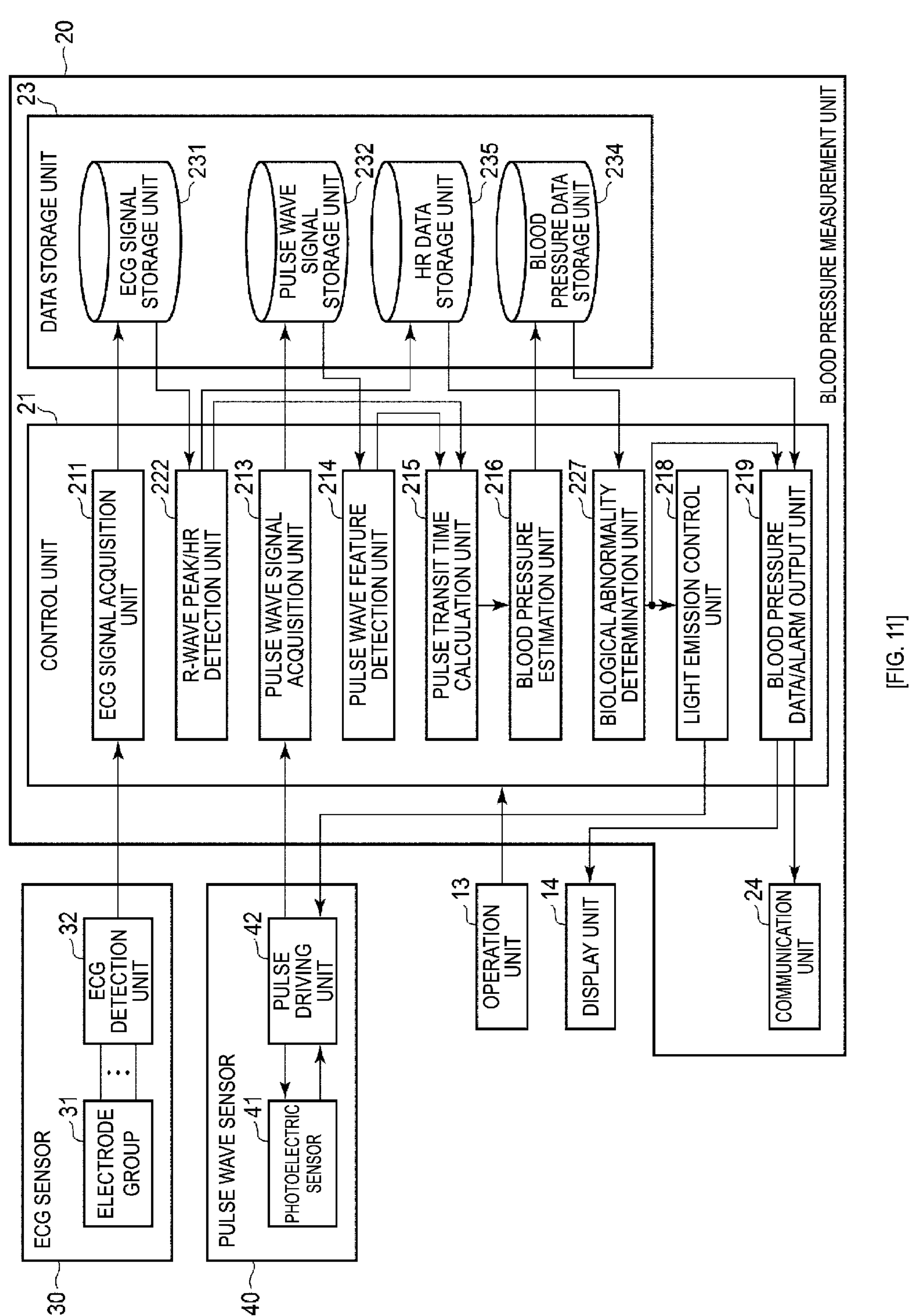
[FIG. 11]

[FIG. 12]
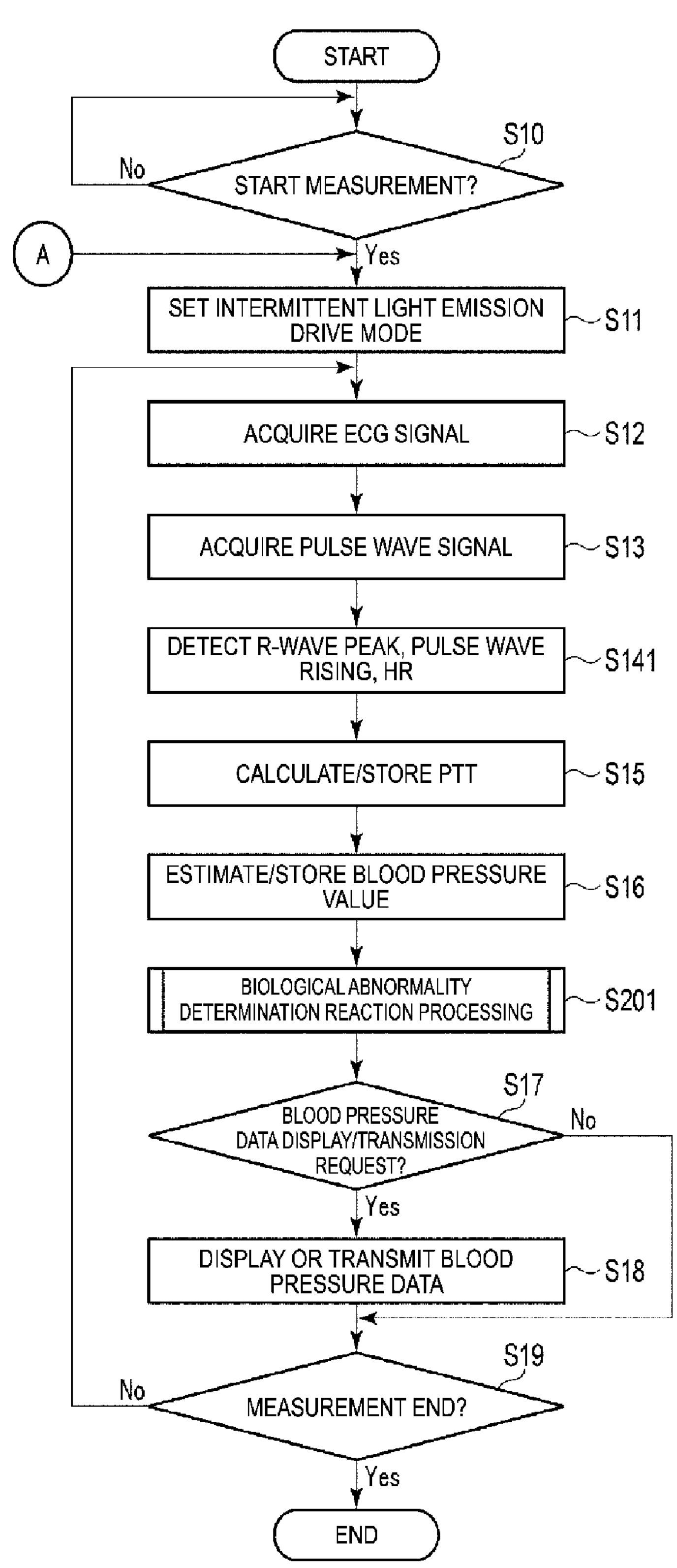

[FIG. 13]

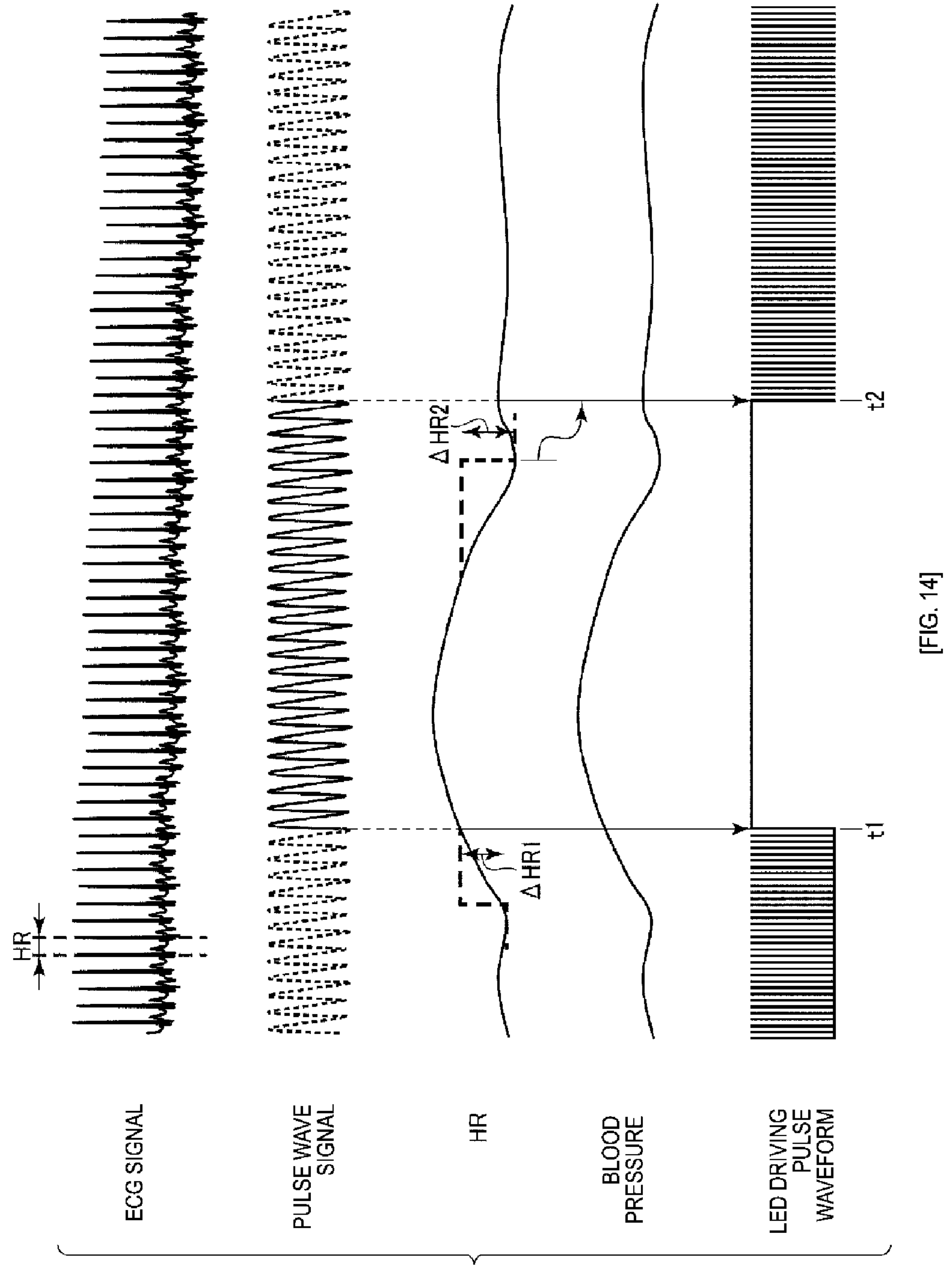
[FIG. 14]

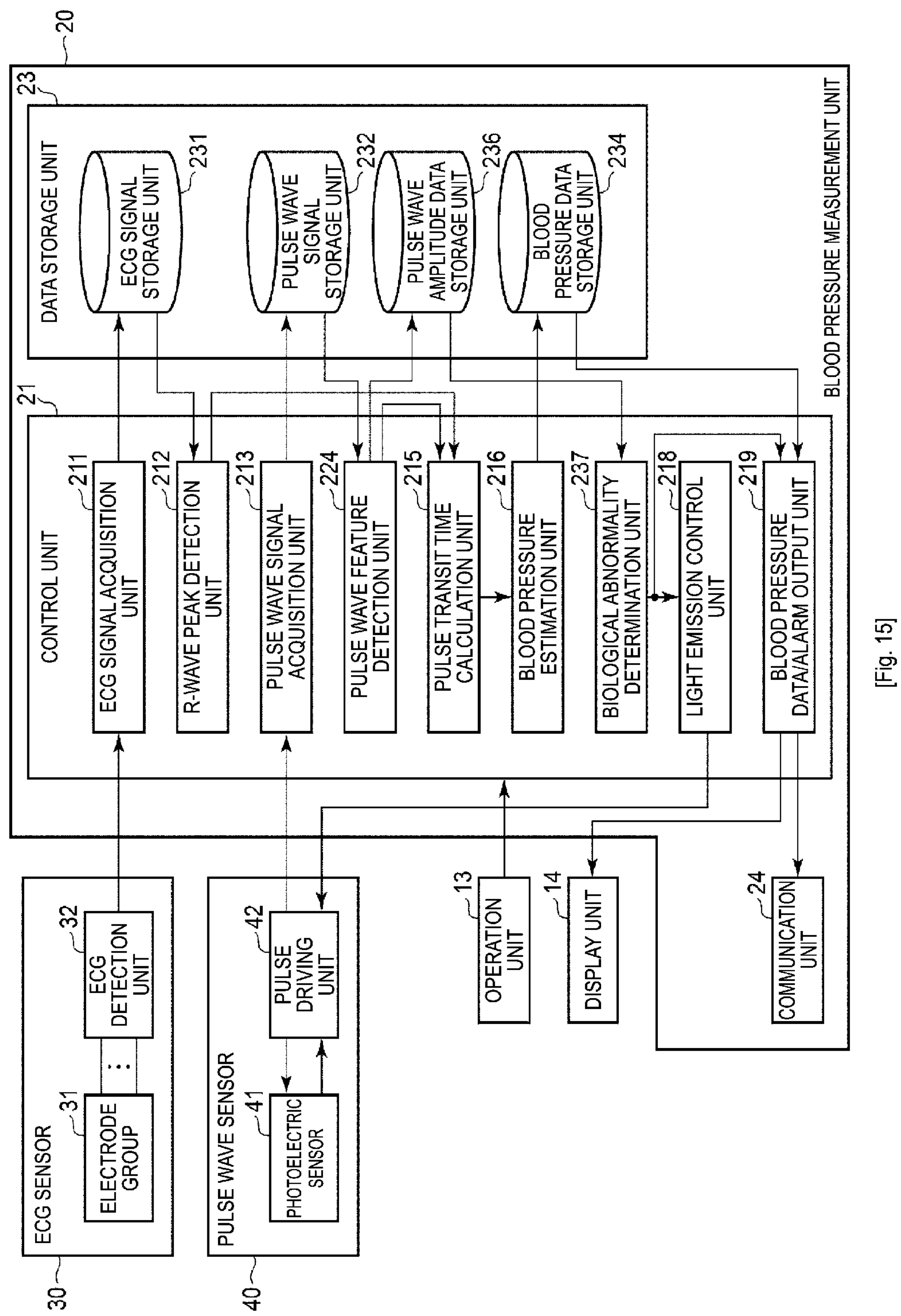
[Fig. 15]

[FIG. 16]
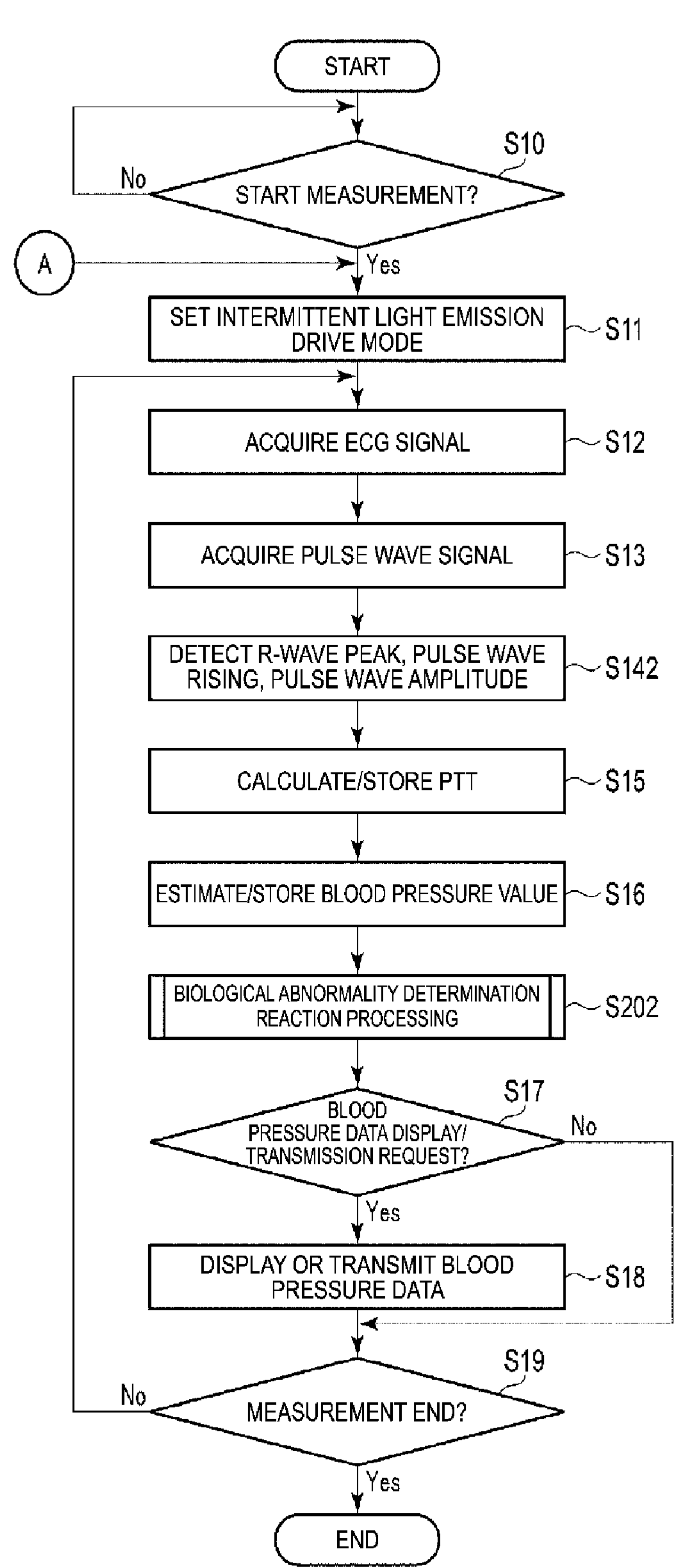

[FIG. 17]

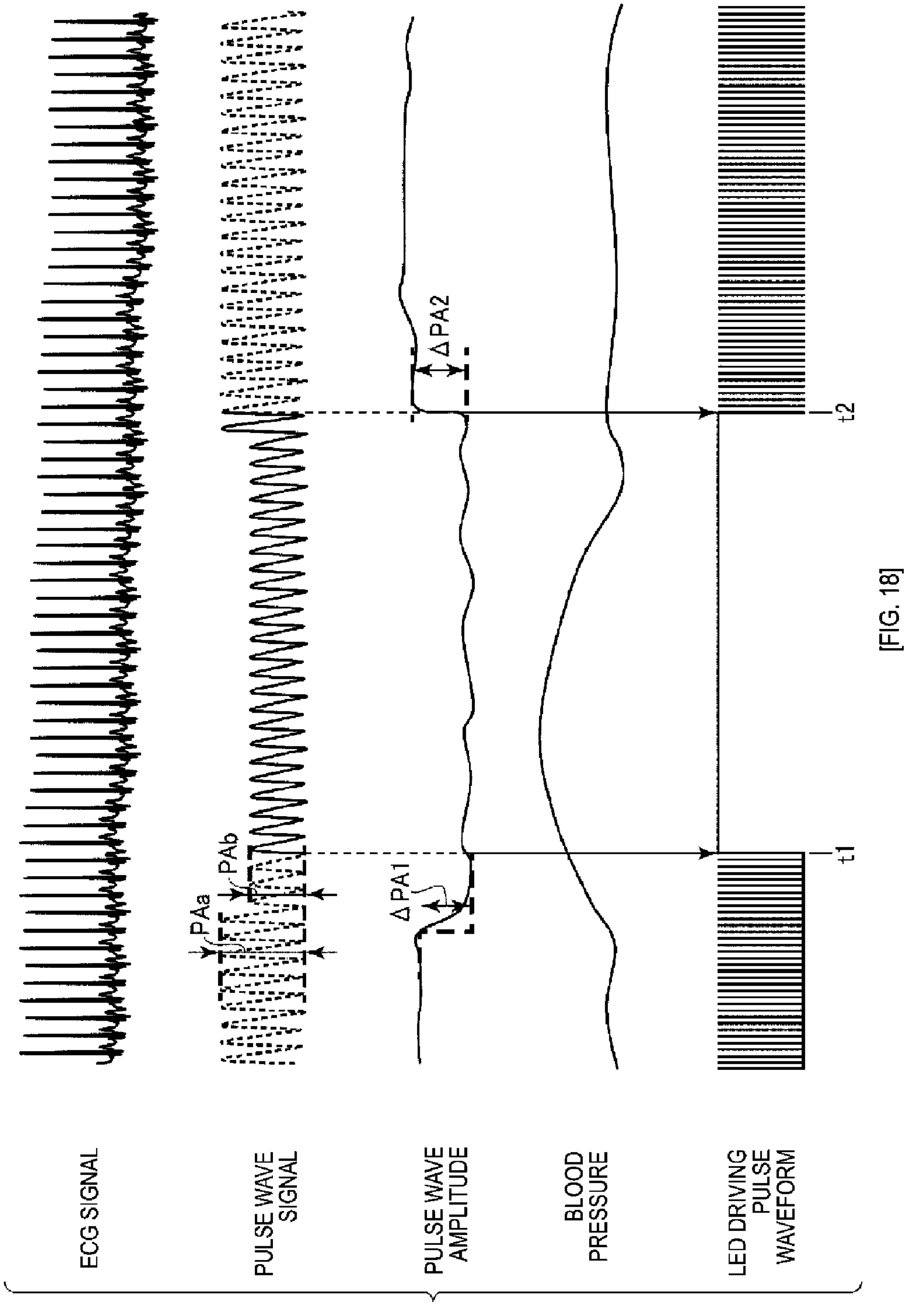
[FIG. 18]

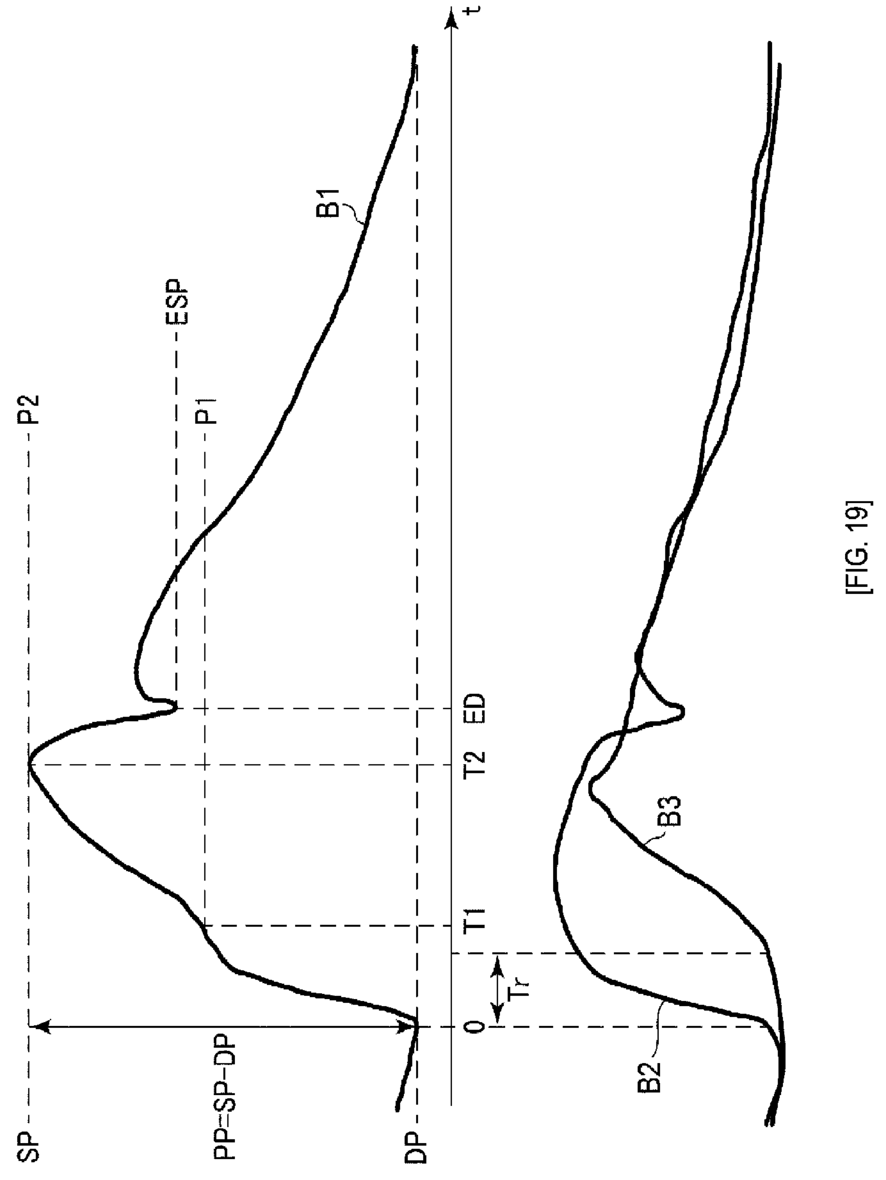
[FIG. 19]

BIOLOGICAL SIGNAL MEASUREMENT DEVICE, METHOD, AND NON-TRANSITORY STORAGE MEDIUM STORING PROGRAM

CROSS-REFERENCE TO RELATED APPLICATIONS

This application is the U.S. national stage application filed pursuant to 35 U.S.C. 365(c) and 120 as a continuation of International Patent Application No. PCT/JP2021/003510, filed Feb. 1, 2021, which application claims priority to Japanese Patent Application No. 2020-027364, filed Feb. 20, 2020, which applications are incorporated herein by reference in their entireties.

TECHNICAL FIELD

An aspect of the present invention relates to a biological signal measurement device, method, and a non-transitory storage medium storing a program for measuring a biological signal of a person, for example.

BACKGROUND

For example, a pulse wave is known as one of biological signals. The pulse wave is a periodic waveform signal generated by the pulsation of the aorta in response to the heartbeat. Pulse wave velocity (PWV) flowing through the artery is correlated with volume elasticity of the blood vessel. The volume elasticity increases as blood pressure increases, and thus the blood pressure as well as the progress of arteriosclerosis can be estimated by obtaining the pulse wave velocity. The pulse wave velocity can be obtained by measuring pulse transit time (PTT) that is time for a pulse wave to transit between two different points on the artery, for example.

As described in Patent Document 1, a known technique of measuring the pulse transit time (PTT) calculates the pulse transit time in measuring the blood pressure based on outputs from an electrocardiogram (ECG) sensor attached to a person's body and a photoelectric sensor applying plethysmography (PPG) attached to the person's ear. As described in Patent Document 2, another known technique also calculates pulse transit time in measuring the blood pressure based on the pulse wave measured by PPG sensors disposed at two different points on the artery.

Unfortunately, the PPG sensor used for measuring the pulse transit time typically uses a light emitting diode (LED) as a light emitting element and thus consumes a larger amount of power than other biometric sensors, such as ECG sensors. Thus, when the blood pressure is measured continuously during sleep (for eight hours for example) by using a blood pressure monitor using, for example, the PPG sensor, the measurement throughout the target measurement period may not be performed due to battery capacity shortage.

In view of this, the present inventors have proposed reducing power consumption by making a light emitting element of a PPG sensor perform an intermittent light emission operation.

Citations: 1. Patent Literature 1: JP 5984088 B; and, 2. Patent Document 2: JP H7-327940.

SUMMARY OF INVENTION

Technical Problem

Unfortunately, making the light emitting element of the PPG sensor perform the intermittent light emission operation can cause no pulse wave to be detected during a period when the light emission operation is not performed, resulting in a lack of blood pressure value measurement data. Thus, when a medical professional or the like attempts to examine in detail later a situation in which an abnormal change in blood pressure of the subject due to a certain cause during, for example, sleeping, the lack of the blood pressure value measurement data may hinder the examination work.

The present invention has been made in view of the above circumstance, and an aspect of the present invention provides a technique enabling biological information to be measured without fail in a case where a condition of a subject changes while suppressing the power consumption.

Solution to the Problem

An aspect of a biological signal measurement device or a biological signal measurement method according to the present invention is configured to acquire a biological signal related to a beat of a heart of a subject from a biometric sensor, detect a feature of the biological signal from the biological signal acquired, determine an abnormal change in the feature based on the feature detected and first threshold information set in advance, set an operation mode of the biometric sensor to a continuous operation mode when the abnormal change in the feature is determined, and set the operation mode of the biometric sensor to an intermittent operation mode in a period without the abnormal change.

Advantageous Effects of the Invention

According to the aspect of the present invention, the biometric sensor operates in an intermittent operation mode when the change in the feature detected from the biological signal is within a normal range, enabling power consumed by the biometric sensor to be suppressed and the continuous use period of the device to be extended. On the other hand, when the change in the feature detected from the biological signal is determined to be abnormal, the operation mode of the biometric sensor is set to the continuous operation mode. Thus, in a state where the feature of the biological signal indicates the abnormal change, the biological signal can be measured without fail, enabling the biological signal to be accurately examined.

Thus, an aspect of the present invention can provide a technique enabling a biological signal to be measured without fail under an abnormality condition while suppressing the power consumption at normal times.

BRIEF DESCRIPTION OF DRAWINGS

The nature and mode of operation of the present invention will now be more fully 5 described in the following detailed description of the invention taken with the accompanying drawing figures, in which:

FIG. 1 is a diagram illustrating an example of an overall configuration of a blood pressure measurement device that is a first embodiment of a biological signal measurement device according to the present invention;

FIG. 2 is a diagram illustrating an example of a configuration on a front surface side of an attachment unit of the blood pressure measurement device illustrated in FIG. 1;

FIG. 3 is a diagram illustrating an example of a configuration on a rear surface side of the attachment unit of the blood pressure measurement device illustrated in FIG. 1;

FIG. 4 is a cross-sectional view illustrating an example of a state in which the attachment unit of the blood pressure measurement device illustrated in FIG. 1 is attached to an upper arm part of a subject;

FIG. 5 is a block diagram illustrating an example of a hardware configuration of the blood pressure measurement device illustrated in FIG. 1;

FIG. 6 is a block diagram illustrating an example of a software configuration of the blood pressure measurement device illustrated in FIG. 1;

FIG. 7 is a flowchart illustrating a procedure and contents of processing executed by a blood pressure measurement unit of the blood pressure measurement device illustrated in FIG. 6;

FIG. 8 is a flowchart illustrating a procedure and contents of biological abnormality determination reaction processing in the flowchart illustrated in FIG. 7;

FIG. 9 is a waveform diagram illustrating a first operation example of the blood pressure measurement device according to the first embodiment of the present invention;

FIG. 10 is a waveform diagram illustrating a second operation example of the blood pressure measurement device according to the first embodiment of the present invention;

FIG. 11 is a block diagram illustrating an example of a software configuration of the blood pressure measurement device according to the second embodiment of the present invention;

FIG. 12 is a flowchart illustrating a procedure and contents of processing executed by a blood pressure measurement unit of the blood pressure measurement device illustrated in FIG. 11;

FIG. 13 is a flowchart illustrating a processing procedure and contents of biological abnormality determination reaction processing in the flowchart illustrated in FIG. 12;

FIG. 14 is a waveform diagram illustrating an operation example of the blood pressure measurement device according to a second embodiment of the present invention;

FIG. 15 is a block diagram illustrating an example of a software configuration of the blood pressure measurement device according to a third embodiment of the present invention;

FIG. 16 is a flowchart illustrating a procedure and contents of processing executed by a blood pressure measurement unit of the blood pressure measurement device illustrated in FIG. 15;

FIG. 17 is a flowchart illustrating a procedure and contents of biological abnormality determination reaction processing in the flowchart illustrated in FIG. 16;

FIG. 18 is a waveform diagram illustrating an operation example of the blood pressure measurement device according to the third embodiment of the present invention; and, FIG. 19 is a diagram illustrating an example of a type of pulse wave feature.

DESCRIPTION OF THE EMBODIMENTS

Embodiments according to one aspect of the present invention will be described below based on the drawings. However, the embodiments described below are merely illustrative of the present invention in all respects.

First Embodiment

Configuration Example, (1) Overall Configuration of Device

FIG. 1 is a diagram illustrating an overall configuration of a blood pressure measurement device that is a first embodiment of a biological signal measurement device according to the present invention. FIGS. 5 and 6 are block diagrams respectively illustrating the hardware configuration and the software configuration of the blood pressure measurement device illustrated in FIG. 1.

The blood pressure measurement device according to the first embodiment includes an attachment unit 10 and a blood pressure measurement unit 20 to be connected to the attachment unit 10. FIG. 1 illustrates a case where the attachment unit 10 and the blood pressure measurement unit 20 is separately configured, but the blood pressure measurement unit 20 and the attachment unit 10 may be integrally provided to function the blood pressure measurement device as a so-called wearable device.

(2) Attachment Unit 10

The attachment unit 10 is attached to an upper arm part 1 of a subject as illustrated in FIG. 1. FIG. 2 illustrates a configuration example on a front surface side of the attachment unit 10, and FIG. 3 illustrates a configuration example on a rear surface side of the attachment unit 10.

The attachment unit 10 includes a belt portion 11 formed of, for example, flexible resin or fiber, and includes an attachment unit circuit unit 12 disposed on a front surface side of the belt portion 11. The attachment unit circuit unit 12 includes an operation unit 13, a display unit 14, an electrocardiographic (ECG) detection unit 32 of an ECG sensor 30 described below, and a pulse driving unit 42 of a pulse wave sensor 40.

The operation unit 13 includes, for example, a push button switch, and is used to input an instruction to start/end the blood pressure measurement, an instruction to display or transmit blood pressure data measured, and the like. The display unit 14 uses, for example, a liquid crystal or organic electro luminescence (EL) as a display device and is used for displaying blood pressure data measured and the like. Note that the operation unit 13 and the display unit 14 may be formed by a tablet device with a sheet for touch panel disposed on a display screen of the display unit.

On the other hand, as illustrated in FIG. 3, an electrode group 31 of the ECG sensor 30 is arranged on the rear surface side of the belt portion 11 in the longitudinal direction of the belt portion 11. The electrode group 31 includes a plurality of (six in this example) electrodes 311 to 316 arranged at an equal interval and is brought in contact with the skin of the subject to detect an ECG signal. As illustrated in FIG. 3, the disposed position of the electrode group 31 in a width direction of the belt portion 11 is set to be close to a shoulder of the subject. This is for enabling the ECG sensor 30 to detect the ECG signal at a position close to the heart of the subject as much as possible.

As illustrated in FIG. 5, the ECG detection unit 32 of the ECG sensor 30 includes a switch circuit 321, a subtraction circuit 322, and an analog front end (AFE) 323. The switch circuit 321 selects two of the six electrodes 311 to 316 to be connected to the subtraction circuit 322, based on a switching control signal output from a control unit 21 of the blood pressure measurement unit 20 described below. The subtraction circuit 322 includes, for example, an instrumentation amplifier, and outputs a potential difference between signals output from the two electrodes selected by the switch circuit 321 as described above. The AFE 323 includes, for example, a low-pass filter (LPF), an amplifier, and an analog-to-digital converter. The LPF removes unwanted noise component from the potential difference signal output from the subtraction circuit 322 as described above. The resultant signal is amplified by the amplifier, and then converted into a digital signal by the analog-to-digital converter. This digital signal obtained by the conversion is output as the ECG signal to the blood pressure measurement unit 20.

On the rear surface side of the belt portion 11, a photoelectric sensor 41 of the pulse wave sensor 40 is disposed at a substantially center portion in the longitudinal direction and the width direction of the belt portion 11. The photoelectric sensor 41 includes a light emitting diode (LED) 411 serving as a light emitting element, and a photo diode (PD) 412 serving as a light receiving element. The LED 411 emits light onto a skin surface of the upper arm part 1. The PD 412 receives reflected light that is the emitted light reflected on the skin surface. An electrical signal corresponding to the intensity of the light thus received is output to the pulse driving unit 42.

The pulse driving unit 42 of the pulse wave sensor 40 includes a current flow and voltage detection circuit 421. The current flow and voltage detection circuit 421 drives the LED 411 for the intermittent or continuous light emission, based on a light emission control signal output from the control unit 21 of the blood pressure measurement unit 20. Of these, the control operation for the intermittent light emission will be described below in detail. The current flow and voltage detection circuit 421 removes a noise component from the electrical signal output from the PD 412, amplifies the resultant signal to a predetermined level, converts the signal into a digital signal, and outputs the pulse wave signal including the digital signal thus converted to the blood pressure measurement unit 20.

Although not illustrated, a loop surface member and a hook surface member forming a surface fastener are attached respectively on the front surface side and the rear surface side of the belt portion 11. With the surface fastener, the attachment unit 10 is fixed with the belt portion 11 wound in a circumferential direction of the upper arm part 1 of the subject. FIG. 4 is a cross-sectional view illustrating an example of a state in which the attachment unit 10 is attached to the upper arm part 1.

(3) Blood Pressure Measurement Unit

The blood pressure measurement unit 20 includes the control unit 21 including a hardware processor such as a central processing unit (CPU), and has a program storage unit 22, a data storage unit 23, and a communication unit 24 connected to the control unit 21. The blood pressure measurement unit 20 includes a power circuit 25.

The communication unit 24 is used to transmit, for example, the measured blood pressure data to an information terminal, which is not illustrated, under the control by the control unit 21. A communication interface to be used includes an interface employing a small power data communication standard, such as Bluetooth (registered trademark). For example, a smartphone or a personal computer is used as the information terminal.

The power circuit 25 generates a required power supply voltage Vcc based on the output of a battery 251 and supplies the generated power supply voltage Vcc to each unit of the blood pressure measurement unit 20 and to the attachment unit circuit unit 12 of the attachment unit 10.

The program storage unit 22, for example, includes a storage medium that is a combination of a non-volatile memory writing and reading to and from which can be performed as needed, such as a hard disk drive (HDD) or a solid state drive (SSD), and a non-volatile memory such as a read only memory (ROM), and stores programs necessary for executing various kinds of control processing according to an embodiment of the present invention, as well as middleware such as an operating system (OS).

The data storage unit 23, for example, includes a storage medium that is a combination of a non-volatile memory writing and reading to and from which can be performed as needed, such as an HDD or an SSD and a volatile memory such as a random access memory (RAM), and includes an ECG signal storage unit 231, a pulse wave signal storage unit 232, a PTT data storage unit 233, and a blood pressure data storage unit 234, as main storage areas for implementing the first embodiment of the present invention.

The ECG signal storage unit 231 is used to chronologically store the ECG signals output from the ECG sensor 30. The pulse wave signal storage unit 232 is used to chronologically store the pulse wave signals output from the pulse wave sensor 40. The PTT data storage unit 233 is used to store PTT calculated by the control unit 21 as described below. The blood pressure data storage unit 234 is used to store blood pressure data estimated by the control unit 21 as described below.

The control unit 21 includes an ECG signal acquisition unit 211, an R-wave peak detection unit 212, and a pulse wave signal acquisition unit 213, a pulse wave feature detection unit 214, and a pulse transit time calculation unit 215, a blood pressure estimation unit 216, a biological abnormality determination unit 217, a light emission control unit 218, and a blood pressure data/alarm output unit 219, as processing functions for implementing the first embodiment of the present invention. Any of these processing units 211 to 219 is implemented by the hardware processor of the control unit 21 executing a program stored in the program storage unit 22.

The ECG signal acquisition unit 211 executes processing of acquiring the ECG signals output from the ECG detection unit 32 of the ECG sensor 30, and temporarily and chronologically storing the acquired ECG signals in the ECG signal storage unit 231. The R-wave peak detection unit 212 executes processing of reading the ECG signal from the ECG signal storage unit 231, and detecting, from the ECG signal, an R-wave peak RP that is one of the features of the ECG signal, for example.

The pulse wave signal acquisition unit 213 executes processing of acquiring pulse wave signals output from the pulse driving unit 42 of the pulse wave sensor 40, and temporarily and chronologically storing the pulse wave signals in the pulse wave signal storage unit 232. The pulse wave feature detection unit 214 executes processing of reading the first pulse wave signal from the pulse wave signal storage unit 232, and detecting, from the pulse wave signal, pulse wave rising PS that is one of the features of the first pulse wave signal, for example.

The pulse transit time calculation unit 215 calculates pulse transit time (PTT) based on a time difference between the R-wave peak RP detected by the R-wave peak detection unit 212 and the pulse wave rising PS detected by the pulse wave feature detection unit 214. Then, the pulse transit time calculation unit 215 executes processing of storing the calculated PTT value in the PTT data storage unit 233.

The blood pressure estimation unit 216 executes processing of estimating a blood pressure value corresponding to the PTT value, by using, for example, a conversion table indicating the relationship between PTT and blood pressure values stored in advance in the data storage unit 23, or by using a conversion formula for the PTT value stored in the PTT data storage unit 233.

The biological abnormality determination unit 217 reads PTT data from the PTT data storage unit 233 and monitors a decrease and increase in the PTT value in a unit period. When a decrease in the PTT value during the unit period reaches or exceeds a threshold set in advance, an abnormality in the PTT value is determined to have occurred. The biological abnormality determination unit 217 determines that the PTT value has been recovered to be within a normal range when the PTT value increases above a threshold set in advance during the unit period after determining the occurrence of the abnormality. Then, the biological abnormality determination unit 217 executes processing of notifying each of the light emission control unit 218 and the blood pressure data/alarm output unit 219 of the determination result.

The light emission control unit 218 controls a light emission control mode of the pulse wave sensor 40 based on the PTT value change determination result thus notified from the biological abnormality determination unit 217. For example, a mode for making the LED 411 of the pulse wave sensor 40 continuously emit light (continuous light emission drive mode) is set for a certain period set in advance from a determination timing of the occurrence of abnormality or for a period to a determination timing of the recovery from the abnormality from the determination timing of the occurrence of the abnormality. On the other hand, a mode for making the LED 411 of the pulse wave sensor 40 intermittently emit light in accordance with a duty ratio set in advance (intermittent light emission drive mode) is set for other periods.

Upon being notified of the result of determination that the abnormality has occurred from the biological abnormality determination unit 217, the blood pressure data/alarm output unit 219 executes processing of monitoring the duration of the abnormality occurring and making a sounder or a speaker (not illustrated) issue an alarm when the duration exceeds a period set in advance.

When a display request for the blood pressure data is input through the operation unit 13, the blood pressure data/alarm output unit 219 executes processing of reading the blood pressure data from the blood pressure data storage unit 234 and displaying the blood pressure data on the display unit 14. When a transmission request for the blood pressure data is input through the operation unit 13, the blood pressure data/alarm output unit 219 executes processing of reading the blood pressure data from the blood pressure data storage unit 234 and transmitting the blood pressure data to the information terminal set in advance to be a transmission destination from the communication unit 24.

(1) Blood Pressure Measurement Using PTT

Next, operations of the blood pressure measurement device configured as described above will be described. Note that this example describes a case where a subject measures a change in the subject's blood pressure while sleeping, for example.

FIG. 7 is a flowchart illustrating a procedure and contents of processing executed by the control unit 21 of the blood pressure measurement unit 20.

First of all, the subject winds the belt portion 11 of the attachment unit 10 around the subject's upper arm part 1 and fixes the attachment unit 10 using the surface fastener, with the belt rear surface side being in contact with the skin surface of the upper arm part 1. In this state, the operation unit 13 provided to the attachment unit 10 is operated to input a measurement start request. This measurement start request also serves as a power ON signal.

In step S10, the blood pressure measurement unit 20 monitors the input of the measurement start request. In this state, when the measurement start request is input from the attachment unit 10, the power circuit 25 operates under the control by the control unit 21 and starts supplying the power supply voltage Vcc to each unit of the device. This results in the blood pressure measurement unit 20 and the attachment unit 10 being in an operating state.

Under the control by the light emission control unit 218, the blood pressure measurement unit 20 in the operating state first sets the intermittent light emission drive mode in step S11. Under the intermittent light emission drive mode, the light emission control unit 218 generates an intermittent light emission control signal and supplies the signal to the pulse driving unit 42 of the pulse wave sensor 40. As a result, the LED 411 is driven by the pulse driving unit 42 to intermittently emit light. Thus, the pulse wave signals detected by the pulse wave sensor 40 are intermittently output.

An intermittent light emission pattern in the intermittent light emission drive mode is set such that only a period corresponding to a single heart rate is the light emitting period and that other periods are the turning-off period for a plurality of heartbeats, for example. The ratio between the light emitting period and the turning-off period of the intermittent light emission pattern, that is, the duty ratio is set to 25%, for example, and the value can be set to be any value based on target power consumption reduction.

In this state, in step S12, the blood pressure measurement unit 20 makes the ECG signal acquisition unit 211 acquire the ECG signals output from the ECG sensor 30 and makes the ECG signal storage unit 231 chronologically store the ECG signals. In step S13, the blood pressure measurement unit 20 makes the pulse wave signal acquisition unit 213 acquire the pulse wave signals output from the pulse wave sensor 40 and makes the pulse wave signal storage unit 232 chronologically store the pulse wave signals.

Then, in step S14, the blood pressure measurement unit 20 makes the R-wave peak detection unit 212 read the ECG signal from the ECG signal storage unit 231, and detect the R-wave peak RP that is one of the features of the ECG signal, and further makes the pulse wave feature detection unit 214 read the pulse wave signal from the pulse wave signal storage unit 232 and detect the pulse wave rising PS that is one of the features of the pulse wave signal.

Then, in step S15, the blood pressure measurement unit 20 makes the pulse transit time calculation unit 215 calculate the time difference between the detection timings of the R-wave peak RP and the pulse wave rising PS detected in a single heart rate, and store the PTT in the PTT data storage unit 233 in the data storage unit 23 as the pulse transit time (PTT) value in the single heart rate.

Then, each time the PTT value in the single heart rate is calculated, the blood pressure measurement unit 20 reads the PTT value from the PTT data storage unit 233 under the control by the blood pressure estimation unit 216 in step S16. Then, a blood pressure value corresponding to the PTT value is estimated by using PTT-blood pressure value conversion table or conversion formula prepared in advance, and the blood pressure data storage unit 234 stores the blood pressure value thus estimated in association with identification information on the heartbeat. As a result, the blood pressure value of a single heartbeat of the subject is stored in the blood pressure data storage unit 234.

(2) Blood Pressure Data Display or Transmission

The blood pressure measurement unit 20 makes the blood pressure data/alarm output unit 219 monitor the input of the blood pressure data display/transmission request in step S17, while executing a series of processes for the blood pressure measurement described above. For example, when the subject operates the operation unit 13 for the display/transmission request, under the control by the blood pressure data/alarm output unit 219, the blood pressure data is read from the blood pressure data storage unit 234 to be displayed on the display unit 14 or transmitted from the communication unit 24 to an information terminal (not illustrated), such as a smartphone, of the subject in step S18.

The blood pressure measurement unit 20 monitors the input of a measurement end request in step S19, while executing the processing for the blood pressure measurement. In this state, when the subject operates the operation unit 13 for the measurement end request, for example, the blood pressure measurement unit 20 ends the processing for the blood pressure measurement and stops the supply of the power supply voltage Vcc to each unit from the power supply circuit 25. The blood pressure data stored in the blood pressure data storage unit 234 is retained even after the end of the power supply.

(3) Determination on and Reaction for Biological Abnormality

While the (1) a series of control for blood pressure measurement and (2) control for blood pressure data display or transmission are being executed, the blood pressure measurement unit 20 determines whether the subject is under biological abnormality in step S20 and executes the corresponding processing for the abnormality as described below under the control by the biological abnormality determination unit 217.

FIG. 8 is a flowchart illustrating an example of a procedure and contents of the above-described biological abnormality determination processing and reaction processing therefor.

First of all, in step S21, the biological abnormality determination unit 217 reads the PTT value over the past unit time (for example, five to six heart rates) set in advance from the PTT data storage unit 233 and calculates a change amount ΔPTT1 in the PTT value read. Then, in step S22, the change amount ΔPTT1 of the PTT value calculated is compared with a first threshold set in advance, and it is determined whether the change amount ΔPTT1 decreases below the first threshold.

Here, it is assumed that the PTT value has changed due to onset of, for example, sleep apnea syndrome and that the change amount ΔPTT1 of the PTT value per unit time has decreased below the first threshold. Then, the biological abnormality determination unit 217 determines that abnormal reduction in PTT value has occurred, and in step S25, changes the operation mode of the pulse wave sensor 40 to the continuous light emission drive mode, and notifies the light emission control unit 218 of the mode. As a result, the light emission control unit 218 outputs the continuous light emission control signal to the pulse driving unit 42 of the pulse wave sensor 40, and then the LED 411 of the photoelectric sensor 41 performs the continuous light emission operation. Thus, the pulse wave sensor 40 continuously detects the pulse wave signals, and the pulse wave signals thus detected continuously are sequentially stored in the pulse wave signal storage unit 232 of the blood pressure measurement unit 20.

When setting the continuous light emission drive mode, in step S26, the biological abnormality determination unit 217 measures the length of the period (abnormal period) during which the state with the reduced PTT value is continuing, and in step S27, determines whether the length of the abnormal period exceeds a threshold Ta set in advance. At the moment when the length of the abnormal period exceeds the threshold Ta, in step S28, an alarm issue instruction is provided to the blood pressure data/alarm output unit 219. As a result, an alarm sound for notification to the subject is issued from, for example, a sounder or a speaker (not illustrated) under the control by the blood pressure data/alarm output unit 219. Making the alarm issue at a point when the abnormal period exceeds the threshold Ta as described above allows the alarm to be prevented from being issued when a temporary PTT change unrelated to biological abnormality occurs.

In step S22, the alarm may be promptly issued at a point when a sharp PTT reduction is detected. Alternatively, the alarm may be issued by means other than sound, such as light emission or blinking of the light emitting element, a warning message displayed on the display unit 14, or vibration. The alarm may also be issued to a terminal of a family member or a medical professional, to notify the family member or the medical professional of the event.

With the continuous light emission operation mode set, in step S23, the biological abnormality determination unit 217 compares a change amount ΔPTT2 of the PTT value per unit time calculated in step S21 with a second threshold set in advance, and determines whether the change amount ΔPTT2 of the PTT value per unit time increases above the second threshold. When, as result of the determination, the change amount ΔPTT2 of the PTT value per unit time has not reached the second threshold, in step S24, the biological abnormality determination unit 217 checks the light emission operation mode being set and maintains the continuous light emission drive mode. Then, the measurement of the length of the abnormal period and the alarm issuing control corresponding to the length in step S26 to S28 are performed.

On the other hand, it is assumed that the biological state of the subject has recovered to a normal breathing state from the SAS state, for example, and that the change amount ΔPTT2 of the PTT value per unit time has increased above the second threshold. Then, in step S29, the biological abnormality determination unit 217 resets the value of the abnormal period measured in step S26 described above, and the processing returns to step S11 illustrated in FIG. 7. In step S11, the light emission operation mode of the pulse wave sensor 40 is changed from the continuous light emission drive mode to the intermittent light emission drive mode.

As a result, the intermittent light emission control signal is output from the light emission control unit 218 of the blood pressure measurement unit 20 to the pulse driving unit 42 of the pulse wave sensor 40. Thus, the light emission operation mode of the LED 411 of the pulse wave sensor 40 returns to the intermittent light emission operation. Accordingly, the pulse wave sensor 40 returns to a low power consumption operation state.

Typical Operation Example

Next, a typical operation example according to the first embodiment will be described. Note that the operation example is not limited to the following example, and various other operation examples are conceivable.

(1) First Operation Example

FIG. 9 is a signal waveform diagram illustrating a first operation example. At normal times, the blood pressure measurement unit 20 drives the pulse wave sensor 40 to intermittently emit light and performs a PTT-based blood pressure measurement operation. The PTT value change amount ΔPTT1 per unit time is monitored during the blood pressure measurement operation.

In this state, it is assumed that the PTT change amount ΔPTT1 per unit time has decreased below the first threshold at time t1. Then, the blood pressure measurement unit 20 determines that an abnormal change in the PTT value due to onset of, for example, sleep apnea syndrome has been detected and changes the light emission operation mode of the LED 411 of the pulse wave sensor 40 from the intermittent light emission drive mode to the continuous light emission drive mode. As a result, the LED 411 of the pulse wave sensor 40 performs the continuous light emission operation, and the pulse wave signals are continuously detected. Thus, the blood pressure measurement unit 20 can thereafter measure the blood pressure value for each heartbeat based on the pulse wave signals continuously detected without fail.

In addition, the blood pressure measurement unit 20 monitors the change amount ΔPTT2 of the PTT value per unit time, in the state where the continuous light emission drive mode is set as described above. Then, when the change amount ΔPTT2 of the PTT value per unit time increases above the second threshold at, for example, time t2, the blood pressure measurement unit 20 determines that the PTT value has recovered to be within a normal range and changes the light emission operation mode of the LED 411 of the pulse wave sensor 40 from the continuous light emission drive mode to the intermittent light emission drive mode.

As a result, the LED 411 of the pulse wave sensor 40 performs the intermittent light emission operation. Thus, the power consumption by the pulse wave sensor 40 is suppressed, whereby the battery 251 can have a longer lasting life. Thus, the blood pressure measurement can be performed for a long period of time without using a large capacity battery.

(2) Second Operation Example

FIG. 10 is a signal waveform diagram illustrating a second operation example. The blood pressure measurement unit 20 measures the duration of the state in which the continuous light emission drive mode is set. Then, the continuous light emission drive mode is maintained until the duration thereof exceeds the threshold, Ta. On the other hand, when the duration of the continuous light emission drive mode exceeds the threshold Ta, the blood pressure measurement unit 20 sets the light emission operation mode of the pulse wave sensor 40 back to the intermittent light emission drive mode. The threshold Ta is set, for example, in accordance with a length of a typical onset time of sleep apnea syndrome, to time longer than the onset time by a predetermined length.

According to this second operation example, the blood pressure measurement unit 20 can make the light emission operation mode of the pulse wave sensor 40 return to the intermittent light emission drive mode, through simple processing with the processing of monitoring the recovery of the PTT value omitted. The threshold may be set to any length in accordance with the period during which the PTT value continues to be abnormal and can be set to infinity in some cases. In such a case, the power consumption of the battery 251 cannot be suppressed, but the blood pressure can be continuously measured over the entire period after the onset and before the battery 251 runs out.

Second Embodiment

Configuration Example. FIG. 11 is a block diagram illustrating a software configuration of a blood pressure measurement device according to a second embodiment of the present invention. The parts in FIG. 11 that are the same as those in FIG. 6 are denoted with the same reference numerals, and the detailed description thereof will be omitted.

The control unit 21 of the blood pressure measurement unit 20 includes an R-wave peak/HR detection unit 222, instead of the R-wave peak detection unit 212 illustrated in FIG. 6. The R-wave peak/HR detection unit 222 detects, from the ECG signal, the R-wave peak and a single heart rate (HR) as the features of the ECG signal.

The data storage unit 23 is provided with an HR data storage unit 235 instead of the PTT data storage unit 233 illustrated in FIG. 6. The HR data storage unit 235 is used to chronologically store individual HRs detected by the ECG sensor 30 as described above.

The biological abnormality determination unit 227 reads HR data from the HR data storage unit 235 and monitors a decrease and increase in an HR value in a unit period. Then, when a change amount ΔHR of the HR value per unit time has increases above a first threshold set in advance, an HR value abnormality is determined to have occurred. The biological abnormality determination unit 227 determines that the HR value has been recovered to be within a normal range when the change amount ΔHR of the HR value per unit time has decreased below a second threshold set in advance after determining the occurrence of abnormality. Then, the biological abnormality determination unit 227 executes processing of notifying each of the light emission control unit 218 and the blood pressure data/alarm output unit 219 of the determination result.

The light emission control unit 218 controls a light emission control mode of the pulse wave sensor 40 based on the result of the determination on the change amount ΔHR of the HR value per unit time thus notified from the biological abnormality determination unit 227. For example, a mode for making the LED 411 of the pulse wave sensor 40 continuously emit light (continuous light emission drive mode) is set for a certain period set in advance from a timing when the abnormal increase of the HR value is detected or for a period until the recovery of the HR value is detected. On the other hand, a mode for making the LED 411 of the pulse wave sensor 40 intermittently emit light in accordance with a duty ratio set in advance (intermittent light emission drive mode) is set for other periods.

Upon being notified of the result of determination that an increase in the change amount ΔHR of the HR value per unit time is abnormal from the biological abnormality determination unit 227, the blood pressure data/alarm output unit 219 executes processing of monitoring the duration of the abnormality of the HR value and making a sounder or a speaker (not illustrated) issue an alarm when the duration exceeds a period Ta set in advance.

Operation Example

Next, operations of the blood pressure measurement device configured as described above will be described.

Note that in this example, a case is described where a subject measures a change in the subject's blood pressure while sleeping, for example.

Figure 13:
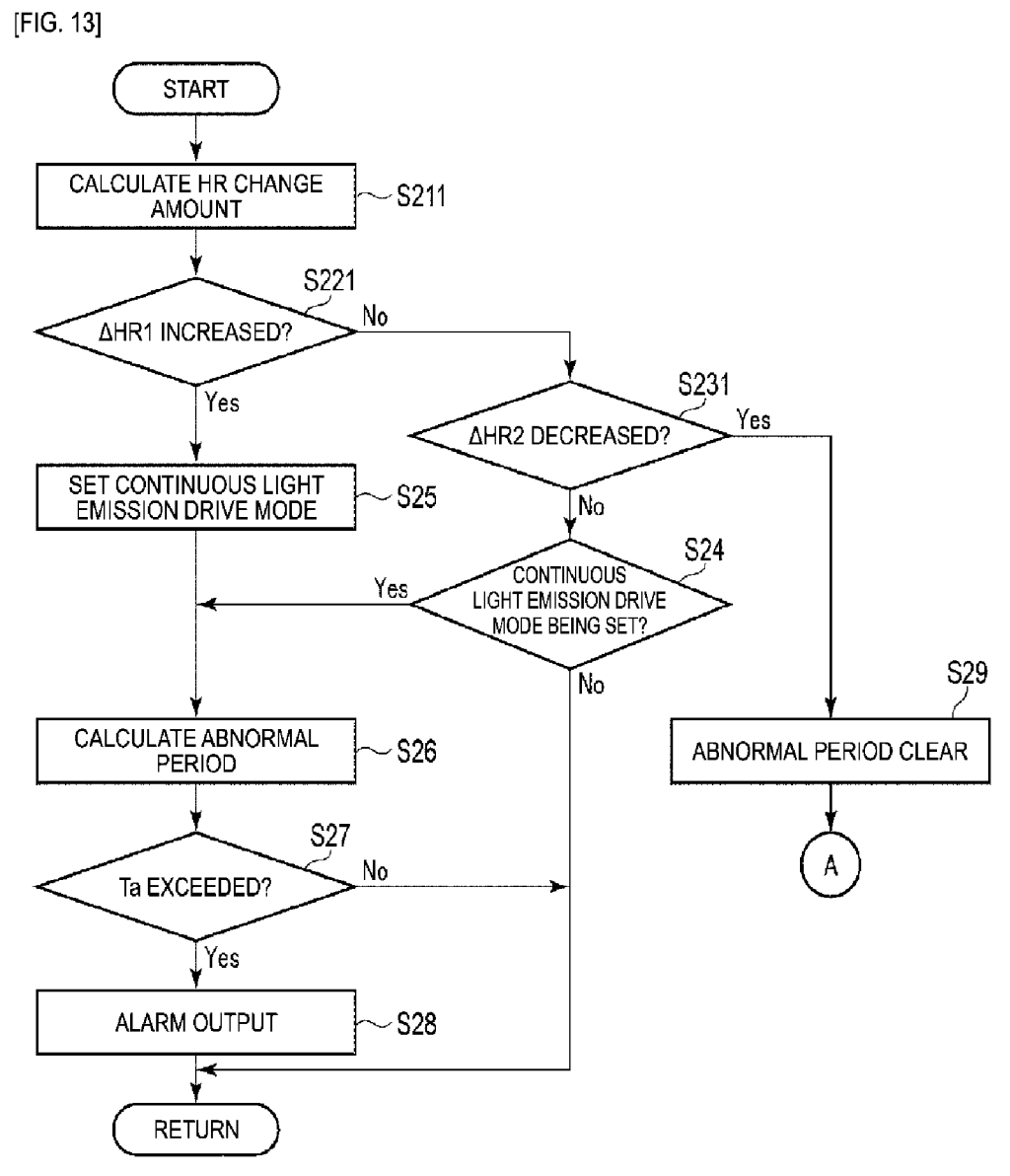

FIGS. 12 and 13 are flowcharts illustrating a procedure and contents of processing executed by the control unit 21 of the blood pressure measurement unit 20. Note that in FIGS. 12 and 13, steps with the contents that are the same as those of the processing in FIGS. 7 and 8 described above will be described while being denoted with the same reference numerals.

When the blood pressure measurement starts, the blood pressure measurement unit 20 first sets the intermittent light emission drive mode in step S11 under the control by the light emission control unit 218. Under the intermittent light emission drive mode, the light emission control unit 218 generates an intermittent light emission control signal and supplies the signal to the pulse driving unit 42 of the pulse wave sensor 40. As a result, the LED 411 is driven by the pulse driving unit 42 to intermittently emit light. Thus, the pulse wave signals detected by the pulse wave sensor 40 are intermittently output.

As in the first embodiment, an intermittent light emission pattern in the intermittent light emission drive mode is set such that only a period corresponding to a single heart rate is the light emitting period and that other periods are the turning-off period for a plurality of heartbeats, for example. The ratio between the light emitting period and the turning-off period of the intermittent light emission pattern, that is, the duty ratio is set to 25%, for example, and the value can be set to be any value based on target power consumption reduction.

In this state, in step S12, the blood pressure measurement unit 20 makes the ECG signal acquisition unit 211 acquire the ECG signals output from the ECG sensor 30 and makes the ECG signal storage unit 231 chronologically store the ECG signals. In step S13, the blood pressure measurement unit 20 makes the pulse wave signal acquisition unit 213 acquire the pulse wave signals output from the pulse wave sensor 40 and makes the pulse wave signal storage unit 232 chronologically store the pulse wave signals.

Then, in step S141, the blood pressure measurement unit 20 makes the R-wave peak/HR detection unit 222 read the ECG signal from the ECG signal storage unit 231 and detect the R-wave peak RP and the HR that are the features of the ECG signal. The HR data storage unit 235 stores the HR thus detected. Meanwhile, the pulse wave feature detection unit 214 reads the pulse wave signal from the pulse wave signal storage unit 232 and detects the pulse wave rising PS which is one of the features of the pulse wave signal.

Then, in step S15, the blood pressure measurement unit 20 makes the pulse transit time calculation unit 215 calculate the time difference between the detection timings of the R-wave peak RP and the pulse wave rising PS detected in a single heart rate, as the pulse transit time (PTT) value in the single heart rate. Then, in step S16, under the control by the blood pressure estimation unit 216, the blood pressure measurement unit 20 estimates a blood pressure value corresponding to the calculated PTT value is estimated by using PTT-blood pressure value conversion table or conversion formula prepared in advance, and the blood pressure data storage unit 234 stores the blood pressure value thus estimated, for example. As a result, the blood pressure value of a single heartbeat of the subject is stored in the blood pressure data storage unit 234.

While executing a series of processing for blood pressure measurement, the blood pressure measurement unit 20 determines, under the control by the biological abnormality determination unit 227, whether the subject is under biological abnormality in step S201 and executes the corresponding processing for the abnormality as described below.

First of all, in step S211, the biological abnormality determination unit 227 reads the HR value over the past unit time (for example, five to six heart rates) set in advance from the HR data storage unit 235 and calculates a change amount ΔHR1 of the HR value thus read. Then, in step S221, the change amount ΔHR1 of the HR value per unit time calculated is compared with a first threshold set in advance, and it is determined whether the change amount ΔHR1 has increased above the first threshold.

Here, it is assumed that due to onset of, for example, sleep apnea syndrome, the change amount ΔHR1 of the HR value per unit time has increased above the first threshold. Then, the biological abnormality determination unit 227 determines that the heart rate has increased abnormally, and in step S25, changes the operation mode of the pulse wave sensor 40 to the continuous light emission drive mode, and notifies the light emission control unit 218 of the mode. As a result, the light emission control unit 218 outputs the continuous light emission control signal to the pulse driving unit 42 of the pulse wave sensor 40, and the LED 411 of the photoelectric sensor 41 performs the continuous light emission operation thereafter. Thus, the pulse wave sensor 40 continuously detects the pulse wave signals, and the pulse wave signals thus detected continuously are sequentially stored in the pulse wave signal storage unit 232 of the blood pressure measurement unit 20.

When setting the continuous light emission drive mode, in step S26, the biological abnormality determination unit 227 measures the length of the period (abnormality duration) during which the HR value abnormality is occurring and determines in step S27 whether the length of the abnormality duration has exceeded the threshold Ta set in advance. At the moment when the duration of the abnormality exceeds the threshold Ta, in step S28, an alarm issue instruction is provided to the blood pressure data/alarm output unit 219. As a result, an alarm sound for notification to the subject is issued from, for example, a sounder or a speaker (not illustrated) under the control by the blood pressure data/alarm output unit 219. Making the alarm thus issue at a point when the abnormality duration exceeds the threshold Ta allows the alarm to be prevented from being issued when a temporary HR change unrelated to biological abnormality occurs.

Note that the above-described alarm may be swiftly issued when a sharp increase in the HR value is detected in step S221. Furthermore, as the alarm, ringing sound, as well as an audio message, light emission, vibration, a warning message displayed on the display unit 14, or the like may be used. The alarm may also be issued to a terminal of a family member or a medical professional, to notify the family member or the medical professional of the event.

With the continuous light emission operation mode set, in step S231, the biological abnormality determination unit 227 compares a change amount ΔHR2 of the HR value per unit time calculated in step S211 with a second threshold set in advance and determines whether a decrease in the change amount ΔHR2 of the HR value per unit time has decreased below the second threshold. When, as result of the determination, the change amount ΔHR2 of the HR value (amount of decrease) per unit time has not reached the second threshold, in step S24, the biological abnormality determination unit 227 checks the light emission operation mode being set and maintains the continuous light emission drive mode. Then, the measurement of the length of the abnormal period and the alarm issuing control corresponding to the length in step S26 to S28 are performed.

On the other hand, it is assumed that the state of the subject has recovered to a normal breathing state from the SAS state, for example, resulting in the change amount ΔHR2 of the HR value per unit time decreasing below the second threshold. Then, in step S29, the biological abnormality determination unit 227 determines that the HR value has been recovered to be within the normal range and resets the value of the abnormality duration measured in step S26 described above. Then, the processing returns to step S11 illustrated in FIG. 12. In step S11, the light emission operation mode of the pulse wave sensor 40 is changed from the continuous light emission drive mode to the intermittent light emission drive mode.

As a result, the intermittent light emission control signal is output from the light emission control unit 218 of the blood pressure measurement unit 20 as the light emission control signal to the pulse driving unit 42 of the pulse wave sensor 40. Thus, the LED 411 of the pulse wave sensor 40 returns to the intermittent light emission operation. Accordingly, the pulse wave sensor 40 returns to a low power consumption operation state.

Typical Operation Example

Next, a typical operation example according to the second embodiment will be described. Note that the operation example is not limited to the following example, and various other operation examples are conceivable.

FIG. 14 is a signal waveform diagram illustrating a typical operation example. At normal times, the blood pressure measurement unit 20 drives the pulse wave sensor 40 to intermittently emit light and performs a PTT-based blood pressure measurement operation. The change amount ΔHR1 of the HR value per unit time is monitored during the blood pressure measurement operation.

In this state, it is assumed that the change amount ΔHR1 of the HR value per unit time has increased above the first threshold at the time t1. Then, for example, the blood pressure measurement unit 20 determines that the heart rate per unit time has abnormally decreased due to onset of, for example, sleep apnea syndrome and changes the light emission operation mode of the LED 411 of the pulse wave sensor 40 from the intermittent light emission drive mode to the continuous light emission drive mode. As a result, the LED 411 of the pulse wave sensor 40 performs the continuous light emission operation, and the pulse wave signals are continuously detected. Thus, the blood pressure measurement unit 20 can thereafter measure the blood pressure value for each heartbeat based on the pulse wave signals continuously detected without fail.

In addition, the blood pressure measurement unit 20 monitors the change amount ΔHR2 of the HR value per unit time, in the state where the continuous light emission drive mode is set as described above. Then, when the change amount ΔHR2 of the HR value per unit time decreases below the second threshold at, for example, the time t2, that is, when the heart rate per unit time has recovered to be within a normal range, the blood pressure measurement unit 20 changes the light emission operation mode of the LED 411 of the pulse wave sensor 40 from the continuous light emission drive mode to the intermittent light emission drive mode. As a result, the LED 411 of the pulse wave sensor 40 performs the intermittent light emission operation. Thus, the power consumption by the pulse wave sensor 40 is suppressed, whereby the battery 251 can have a longer lasting life. Thus, the blood pressure measurement can be performed for a long period of time without using a large capacity battery.

Third Embodiment

Configuration Example. FIG. 15 is a block diagram illustrating a software configuration of a blood pressure measurement device according to a third embodiment of the present invention. The parts in FIG. 15 that are the same as those in FIG. 6 are denoted with the same reference numerals, and the detailed description thereof will be omitted.

A pulse wave feature detection unit 224 provided to the control unit 21 of the blood pressure measurement unit 20 detects each of the pulse wave rising PS and a pulse wave amplitude PA from a pulse wave signal stored in the pulse wave signal storage unit 232, as features of the pulse wave signal.

The data storage unit 23 is provided with a pulse wave amplitude data storage unit 236 instead of the PTT data storage unit 233 illustrated in FIG. 6. The pulse wave amplitude data storage unit 236 is used to chronologically store the pulse wave amplitudes PA detected by the pulse wave feature detection unit 224.

A biological abnormality determination unit 237 reads pulse wave amplitude data from the pulse wave amplitude data storage unit 236 and monitors a change amount ΔPA of the pulse wave amplitude PA per unit time. Then, when the change amount ΔPA of the pulse wave amplitude PA per unit time has decreased below a first threshold set in advance, an abnormality in the pulse wave amplitude PA is determined to have occurred. The biological abnormality determination unit 237 determines that the pulse wave amplitude PA has been recovered to be within a normal range when the change amount ΔPA of the pulse wave amplitude PA per unit time has increased above a second threshold set in advance after determining the occurrence of abnormality. Then, the biological abnormality determination unit 237 executes processing of notifying each of the light emission control unit 218 and the blood pressure data/alarm output unit 219 of the determination result.

The light emission control unit 218 controls a light emission control mode of the pulse wave sensor 40 based on the result of the determination on the change amount ΔPA of the pulse wave amplitude PA per unit time thus notified from the biological abnormality determination unit 237. For example, a mode for making the LED 411 of the pulse wave sensor 40 continuously emit light (continuous light emission drive mode) is set for a certain period set in advance from a timing when the abnormal decrease of the pulse wave amplitude PA is detected or for a period until the recovery of the pulse wave amplitude PA is detected. On the other hand, a mode for making the LED 411 of the pulse wave sensor 40 intermittently emit light in accordance with a duty ratio set in advance (intermittent light emission drive mode) is set for other periods.

Upon being notified of the result of determination that a decrease in the change amount ΔPA of the pulse wave amplitude PA per unit time is abnormal from the biological abnormality determination unit 237, the blood pressure data/alarm output unit 219 executes processing of monitoring the abnormality duration of the pulse wave amplitude PA and making a sounder or a speaker (not illustrated) issue an alarm when the duration exceeds a period Ta set in advance.

Operation Example

Next, operations of the blood pressure measurement device configured as described above will be described.

Note that in this example, a case is described where a subject measures a change in the subject's blood pressure while sleeping, for example.

Figure 17:
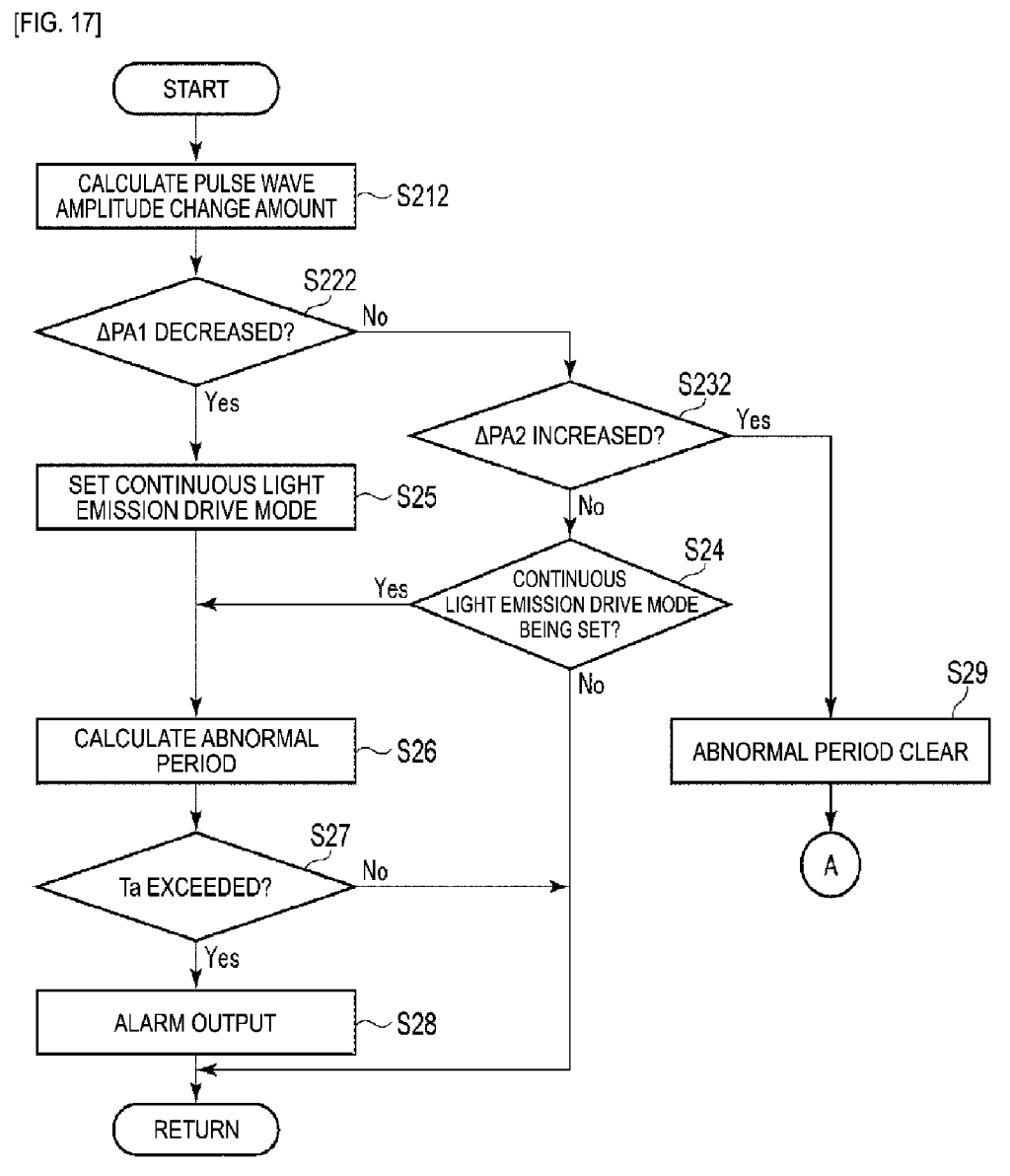

FIGS. 16 and 17 are flowcharts illustrating a procedure and contents of processing executed by the control unit 21 of the blood pressure measurement unit 20. Note that in FIGS. 16 and 17, steps with the contents that are the same as those of the processing in FIGS. 7 and 8 described above will be described while being denoted with the same reference numerals.

When the blood pressure measurement starts, the blood pressure measurement unit 20 first sets the intermittent light emission drive mode in step S11 under the control by the light emission control unit 218. Under the intermittent light emission drive mode, the light emission control unit 218 generates an intermittent light emission control signal and supplies the signal to the pulse driving unit 42 of the pulse wave sensor 40. As a result, the LED 411 is driven by the pulse driving unit 42 to intermittently emit light. Thus, the pulse wave signals detected by the pulse wave sensor 40 are intermittently output.

As in the first and the second embodiments, an intermittent light emission pattern in the intermittent light emission drive mode is set such that only a period corresponding to a single heart rate is the light emitting period and that other periods are the turning-off period for a plurality of heartbeats, for example. The ratio between the light emitting period and the turning-off period of the intermittent light emission pattern, that is, the duty ratio is set to 25%, for example, and the value can be set to be any value based on target power consumption reduction.

In this state, in step S12, the blood pressure measurement unit 20 makes the ECG signal acquisition unit 211 acquire the ECG signals output from the ECG sensor 30 and makes the ECG signal storage unit 231 chronologically store the ECG signals. In step S13, the blood pressure measurement unit 20 makes the pulse wave signal acquisition unit 213 acquire the pulse wave signals output from the pulse wave sensor 40 and makes the pulse wave signal storage unit 232 chronologically store the pulse wave signals.

Then, in step S142, the blood pressure measurement unit 20 makes the R-wave peak detection unit 212 read the ECG signal from the ECG signal storage unit 231 and detect the R-wave peak RP that is a feature of the ECG signal. Meanwhile, the pulse wave feature detection unit 224 reads the pulse wave signal from the pulse wave signal storage unit 232 and detects the pulse wave rising PS and the pulse wave amplitude PA, which are the features of the pulse wave signal. The pulse wave amplitude data storage unit 236 chronologically stores the values of the pulse wave amplitude PA detected.

Then, in step S15, the blood pressure measurement unit 20 makes the pulse transit time calculation unit 215 calculate the time difference between the detection timings of the R-wave peak RP and the pulse wave rising PS detected in a single heart rate, as the pulse transit time (PTT) value in the single heart rate. Then, in step S16, under the control by the blood pressure estimation unit 216, the blood pressure measurement unit 20 estimates a blood pressure value corresponding to the calculated PTT value is estimated by using, for example, PTT-blood pressure value conversion table or conversion formula prepared in advance, and the blood pressure data storage unit 234 stores the blood pressure value thus estimated. As a result, the blood pressure value of a single heartbeat of the subject is stored in the blood pressure data storage unit 234.

While executing a series of processing for blood pressure measurement, the blood pressure measurement unit 20 determines whether the subject is under biological abnormality in step S202 and executes the corresponding processing for the abnormality as described below under the control by the biological abnormality determination unit 237.

First of all, in step S212, the biological abnormality determination unit 237 reads the pulse wave amplitude PA over the past unit time (for example, five to six heart rates) set in advance from the pulse wave amplitude data storage unit 236 and calculates a change amount ΔPA1 in the pulse wave amplitude PA thus read. Then, in step S222, the change amount ΔPA of the pulse wave amplitude PA1 per unit time calculated is compared with a first threshold set in advance, and it is determined whether the change amount ΔPA1 has decreased below the first threshold.

In this state, is assumed that the change amount ΔPA1 of the pulse wave amplitude PA per unit time has decreased below the first threshold due to occurrence of a certain biological abnormality, for example. Then, the biological abnormality determination unit 237 changes in step S25, the operation mode of the pulse wave sensor 40 to the continuous light emission drive mode and notifies the light emission control unit 218 of the mode. As a result, the light emission control unit 218 outputs the continuous light emission control signal to the pulse driving unit 42 of the pulse wave sensor 40, and the LED 411 of the photoelectric sensor 41 performs the continuous light emission operation thereafter. Thus, the pulse wave sensor 40 continuously detects the pulse wave signals, and the pulse wave signals thus detected continuously are sequentially stored in the pulse wave signal storage unit 232 of the blood pressure measurement unit 20.

When setting the continuous light emission drive mode, in step S26, the biological abnormality determination unit 237 measures the length of the period (abnormality duration) during which the abnormality of the pulse wave amplitude PA is occurring and determines in step S27 whether the length of the abnormality duration has exceeded the threshold Ta set in advance. When the abnormality duration exceeds the threshold Ta, in step S28, an alarm issue instruction is provided to the blood pressure data/alarm output unit 219. As a result, an alarm sound for notification to the subject is issued from, for example, a sounder or a speaker (not illustrated) under the control by the blood pressure data/alarm output unit 219. Making the alarm thus issue at a point when the abnormality duration exceeds the threshold Ta allows the alarm to be prevented from being issued when a temporary PA change unrelated to biological abnormality occurs.

Note that the above-described alarm may be swiftly issued when a sharp decrease in the pulse wave amplitude PA is detected in step S222. Furthermore, as the alarm, ringing sound, as well as an audio message, light emission, vibration, a warning message displayed on the display unit 14, or the like may be used. The alarm may also be issued to a terminal of a family member or a medical professional, to notify the family member or the medical professional of the event.

With the continuous light emission operation mode set, in step S232, the biological abnormality determination unit 237 compares a change amount ΔPA2 of the pulse wave amplitude PA per unit time calculated in step S212 with a second threshold set in advance and determines whether the change amount ΔPA2 of the pulse wave amplitude PA per unit time has increased above the second threshold. When, as result of the determination, the change amount ΔPA2 (amount of increase) in the pulse wave amplitude PA per unit time has not reached the second threshold, in step S24, the biological abnormality determination unit 237 checks the light emission operation mode being set and maintains the continuous light emission drive mode. Then, the measurement of the length of the abnormal period and the alarm issuing control corresponding to the length in step S26 to S28 are performed.

On the other hand, it is assumed that the biological state of the subject has recovered to a normal state, for example, resulting in the change amount ΔPA2 of the pulse wave amplitude PA per unit time increasing above the second threshold. Then, in step S29, the biological abnormality determination unit 237 determines that the pulse wave amplitude PA has been recovered to be within the normal range and resets the value of the abnormality duration that is being measured in step S26 described above. Then, the processing returns to step S11 illustrated in FIG. 12. In step S11, the light emission operation mode of the pulse wave sensor 40 is changed from the continuous light emission drive mode to the intermittent light emission drive mode.

As a result, the intermittent light emission control signal is output from the light emission control unit 218 of the blood pressure measurement unit 20 as the light emission control signal to the pulse driving unit 42 of the pulse wave sensor 40. Thus, the LED 411 of the pulse wave sensor 40 returns to the intermittent light emission operation. Accordingly, the pulse wave sensor 40 returns to a low power consumption operation state.

Typical Operation Example

Next, a typical operation example according to the third embodiment will be described. Note that the operation example is not limited to the following example, and various other operation examples are conceivable.

FIG. 18 is a signal waveform diagram illustrating a typical operation example.

At normal times, the blood pressure measurement unit 20 drives the pulse wave sensor 40 to intermittently emit light and performs a PTT-based blood pressure measurement operation. The change amount ΔPA1 of the pulse wave amplitude PA per unit time is monitored during the blood pressure measurement operation.

In this state, it is assumed that the increase in the change amount ΔPA1 of the pulse wave amplitude PA per unit time has increased above the first threshold at the time t1. Then, for example, the blood pressure measurement unit 20 determines that a biological abnormality has occurred in the subject and changes the light emission operation mode of the LED 411 of the pulse wave sensor 40 from the intermittent light emission drive mode to the continuous light emission drive mode. As a result, the LED 411 of the pulse wave sensor 40 performs the continuous light emission operation, and the pulse wave signals are continuously detected. Thus, the blood pressure measurement unit 20 can thereafter measure the blood pressure value for each heartbeat based on the pulse wave signals continuously detected without fail.

In addition, the blood pressure measurement unit 20 monitors the change amount ΔPA2 of the pulse wave amplitude PA per unit time, in the state where the continuous light emission drive mode is set as described above. Then, when the change amount ΔPA2 of the pulse wave amplitude PA per unit time exceeds the second threshold at, for example, the time t2, that is, when the pulse wave amplitude PA is recovered to be within a normal range, the light emission operation mode of the LED 411 of the pulse wave sensor 40 is returned from the continuous light emission drive mode to the intermittent light emission drive mode. As a result, the LED 411 of the pulse wave sensor 40 performs the intermittent light emission operation. Thus, the power consumption by the pulse wave sensor 40 is suppressed, whereby the battery 251 can have a longer lasting life. Thus, the blood pressure measurement can be performed for a long period of time without using a large capacity battery.

Other Embodiments

In the case described as an example in the third embodiment above, the pulse wave amplitude PA is detected as the pulse wave feature for detecting the biological abnormality. Alternatively, the following other features may be detected as the pulse wave feature. FIG. 19 is a diagram illustrating example pulse waveforms B1, B2, and B3 and types of the pulse wave feature of the same. Note that these types of pulse wave feature are described as an example in Japanese Translation of PCT International Application Publication No. JP-T-2018-517528 A.

Specifically, the pulse wave feature includes a period T1 from the rising to a first peak P1 of the pulse wave, a period T2 from the rising to a second peak P2 of the pulse wave, reciprocal 1/T1 of the period T1 to the first peak P1, reciprocal 1/T2 of the period T2 to the second peak P2, a period (T2−T1) from the first peak P1 to the second peak P2, a period Tr until reflection, ejection period ED, a ratio between an amplitude PP (SP−DP) of the second peak P2 and T2, (P2−DP)/(P1−DP), (P1−DP)/(P2−DP), and the like.

As types of biological signal related to the heartbeat, in addition to the ECG signal or the pulse wave signal, a skin impedance changing in accordance with the vibration of the blood vessel and the like may be detected. Furthermore, the configuration, the processing procedure, and the processing content of the biological signal measurement device as well as the configuration of the light emission control pattern of the light emitting element of the pulse wave sensor and the like may be modified in various ways without departing from the gist of the present invention.

While the embodiments according to the present invention have been described in detail above, the above-described description merely exemplifies the present invention in all respects, and obviously, various improvements and modifications can be made without departing from the scope of the present invention. That is, specific configurations according to the respective embodiment may be employed as appropriate in the implementation of the present invention.

Additionally, in the present invention, various inventions can be formed by appropriately combining a plurality of components disclosed in the embodiments described above. For example, some components may be omitted from all the components described in the respective embodiments. Further, the components of the different embodiments may be combined appropriately.

Note that the present invention is not limited to the above-described embodiments, and various modifications can be made in an implementation stage without departing from the gist. Further, embodiments may be carried out as appropriate in a combination, and combined effects can be obtained in such case. Further, the various inventions are included in the embodiment, and the various inventions may be extracted in accordance with combinations selected from the plurality of disclosed components. For example, in a case where the problem can be solved and the effects can be obtained even when some components are removed from the entire components given in the embodiment, the configuration obtained by removing the components may be extracted as an invention.

REFERENCE NUMERALS LIST

1 Upper arm part
2 Bone part
3 Artery
10 Attachment unit
11 Belt portion
12 Attachment unit circuit unit
13 Operation unit
14 Display unit
20 Blood pressure measurement unit
21 Control unit
22 Program storage unit
23 Data storage unit
24 Communication unit
25 Power circuit
211 ECG signal acquisition unit
212 R-wave peak detection unit
213 Pulse wave signal acquisition unit
214, 224 Pulse wave feature detection unit
215 Pulse transit time calculation unit
216 Blood pressure estimation unit
217, 227, 237 Biological abnormality determination unit
218 Light emission control unit
219 Blood pressure data/alarm output unit
222 R-wave peak/HR detection unit
231 ECG signal storage unit
232 Pulse wave signal storage unit
233 PTT data storage unit
234 Blood pressure data storage unit
235 HR data storage unit
236 Pulse wave amplitude data storage unit
251 Battery
30 ECG sensor
31 Electrode group
32 ECG detection unit
321 Switch circuit
322 Subtraction circuit
323 AFE
40 Pulse wave sensor
41 Photoelectric sensor
411 LED
412 PD
42 Pulse driving unit
421 Energization and voltage detection circuit

What is claimed is:

1. A biological signal measurement device, comprising:
a processor configured to:
acquire a biological signal related to a beat of a heart of a subject from a biometric sensor;
detect a feature related to the beat of the heart from the biological signal acquired;
compare a change amount of the feature detected per unit time with a threshold defined in first threshold information set in advance, and determine an abnormal change has occurred in the feature when the change amount decreases below the threshold defined in the first threshold information;
set an operation mode of the biometric sensor to a continuous operation mode when it is determined that the abnormal change has occurred in the feature;
set the operation mode of the biometric sensor to an intermittent operation mode in periods when no abnormal change is determined;
determine that the feature has returned to a normal range when the feature satisfies a second threshold information set in advance;
monitor an abnormal duration from a time when the abnormal change has occurred, the abnormal duration being a duration of the continuous operation mode, and changes the operation mode of the biometric sensor from the continuous operation mode to the intermittent operation mode when the duration exceeds a period set in advance;
reset the abnormal duration and change the operation mode to the intermittent operation mode when it is determined that the feature has returned to the normal range while in the continuous operation mode; and
change the operation mode to the intermittent operation mode when the abnormal duration exceeds a preset period.

2. The biological signal measurement device according to claim 1, wherein
the processor is further configured to determine the abnormal change in the feature has occurred when a change amount of the feature per unit time exceeds a second threshold defined in the first threshold information.

3. The biological signal measurement device according to claim 1 further comprising
the processor is configured to;
determine a change of the feature to be within a normal range based on the feature detected and second threshold information set in advance, and
change the operation mode of the biometric sensor to the intermittent operation mode when the feature has changed to be within the normal range in a state where the operation mode of the biometric sensor is set to the continuous operation mode.

4. The biological signal measurement device according to claim 1, wherein
the processor further detects, as the feature of the biological signal, any of pulse wave velocity in a blood vessel, heart rate of the heart per unit time, and a feature of a pulse wave.

5. The biological signal measurement device according to claim 1, wherein the processor is further configured to generate and output notification information for notifying the subject of the abnormal change in the feature.

6. A non-transitory storage medium storing a program that causes a processor provided in the biological signal measurement device according to claim 1 to execute processing the biological signal measurement.

7. The biological signal measurement device according to claim 4 further comprising
the processor configured to generate and output notification information for notifying the subject of the abnormal change in the feature in response to a result of the abnormal change in the feature.

* * * * *